United States Patent [19]

Malek et al.

[11] Patent Number: 5,130,238
[45] Date of Patent: Jul. 14, 1992

[54] ENHANCED NUCLEIC ACID AMPLIFICATION PROCESS

[75] Inventors: Lawrence T. Malek, Brampton; Cheryl Davey, Toronto; Graham Henderson, Mississauga; Roy Sooknanan, Toronto, all of Canada

[73] Assignee: Cangene Corporation, Mississauga, Canada

[21] Appl. No.: 397,681

[22] Filed: Aug. 23, 1989

Related U.S. Application Data

[63] Continuation-in-part of Ser. No. 211,384, Jun. 24, 1988.

[51] Int. Cl.$^5$ .................. C12P 19/34; C12Q 1/68; C07H 15/12; C07H 17/00
[52] U.S. Cl. .................................. 435/91; 435/6; 435/172.3; 435/810; 436/94; 436/508; 536/27; 536/28
[58] Field of Search .................. 435/6, 91; 536/27

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |

FOREIGN PATENT DOCUMENTS

| | | |
|---|---|---|
| 0200362 | 12/1986 | European Pat. Off. |
| 0201184 | 12/1986 | European Pat. Off. |
| 310229 | 4/1989 | European Pat. Off. |
| 373960 | 6/1990 | European Pat. Off. |
| 8810315 | 12/1988 | PCT Int'l Appl. ............ 435/6 |
| 8901050 | 2/1989 | PCT Int'l Appl. ............ 435/6 |
| WO82/00158 | 1/1982 | World Int. Prop. O. |
| WO87/06170 | 10/1987 | World Int. Prop. O. |
| WO88/10315 | 12/1988 | World Int. Prop. O. |
| WO89/01050 | 2/1989 | World Int. Prop. O. |

OTHER PUBLICATIONS

Davanloo et al Proc Natl Acad Sci 81:2035-39 (1984).
Scapes *Protein Purification* (1982) Springer-Verlag New York Inc. NY NY p. 197.
Bethesda Research Laboratories Catalogue of 1988 Bethesda, M.D. pp. 30 and 37.
Gelfand et al. "Principles and Applications for DNA Amplification", *PCR Technologies*, Stockton Press, New York (1989).
Scharf et al. "Direct Cloning and Sequence Analysis of Enzymatically Amplified Genomic Sequences", *Science*, 233:1076-1078 (1976).
Maniatis et al. Molecular Cloning—A Laboratory manual (Cold Spring Harbor Laboratory 1982).
Okayama et al. "High-Efficiency Cloning of Full-Length cDNA", *Mol. Cel. Biol.*, 2:161 (1982).
Gubler et al. "A Simple and Very Efficient Method for Generating cDNA Libraries", *Gene*, 25:263-269 (1983).
Polites et al. "A Step-Wise Protocol for cDNA Synthesis", *Bio Techniques* 4:514 (1986).

*Primary Examiner*—Margaret Moskowitz
*Assistant Examiner*—Scott A. Chambers
*Attorney, Agent, or Firm*—Foley & Lardner

[57] ABSTRACT

This invention relates to an improved process for amplifying a specific nucleic acid sequence. The process involves synthesizing single-stranded RNA, single-stranded DNA and Double-stranded DNA. The single-stranded RNA is a first template for a first primer, the single-stranded DNA is a second template for a second primer, and the double stranded DNA is a third template for synthesis of a plurality of copies of the first template. A sequence of the first primer or the second primer is complementary to a sequence of the specific nucleic acid and a sequence of the first primer or the second primer is homologous to a sequence of the specific nucleic acid. The improvement of the amplification process involves the addition of DMSO alone or in combination with BSA, which improves the specificity and efficiency of the amplification. The amplification process may be used to increase the quantity of a specific nucleic acid sequence to allow detection, or to increase the purity of a specific nucleic acid sequence as a substitute for conventional cloning methodology.

47 Claims, 11 Drawing Sheets

FIG. 1B

| | | | | | | | |
|---|---|---|---|---|---|---|---|
| NATURAL RNA TARGET | 5' | nnn | C | B | A | nnnnnnnnnn | 3' |
| 1st OLIGO. PRIMER | 3' | | | | a' | i' | p' | 5' |

1. REVERSE TRANSCRIPTASE + dNTP's

| | | | | | | | |
|---|---|---|---|---|---|---|---|
| NATURAL RNA TARGET | 5' | nnn | C | B | A | nnnnnnnnnn | 3' |
| 1st DNA SEGMENT | 3' | nnn | c' | b' | a' | i' | p' | 5' |

2. RIBONUCLEASE H

| | | | | | | | |
|---|---|---|---|---|---|---|---|
| 1st DNA SEGMENT | 3' | nnn | c' | b' | a' | i' | p' | 5' |

3. PRIMING

| | | | | | | | |
|---|---|---|---|---|---|---|---|
| 2nd OLIGO. PRIMER | 5' | | C | | | | | 3' |
| 1st DNA SEGMENT | 3' | nnn | c' | b' | a' | i' | p' | 5' |

4. REVERSE TRANSCRIPTASE + dNTP's

| | | | | | | | |
|---|---|---|---|---|---|---|---|
| 2nd DNA SEGMENT | 5' | | C | B | A | I | P | 3' |
| 1st DNA SEGMENT | 3' | nnn | c' | b' | a' | i' | p' | 5' |

5. T7 RNA POLYMERASE + NTP's

| | | | | | | |
|---|---|---|---|---|---|---|
| RNA PRODUCT | 3' | c' | b' | a' | i' | | 5' |

6. PRIMING

| | | | | | | |
|---|---|---|---|---|---|---|
| 2nd OLIGO. PRIMER | 5' | C | | | | | 3' |
| RNA PRODUCT | 3' | c' | b' | a' | i' | | 5' |

7. REVERSE TRANSCRIPTASE + dNTP's

| | | | | | | |
|---|---|---|---|---|---|---|
| 2nd DNA SEGMENT | 5' | C | B | A | I | | 3' |
| RNA PRODUCT | 3' | c' | b' | a' | i' | | 5' |

8. RIBONUCLEASE H

| | | | | | | | |
|---|---|---|---|---|---|---|---|
| 2nd DNA SEGMENT | 5' | C | B | A | I | P | 3' |

9. PRIMING

| | | | | | | | |
|---|---|---|---|---|---|---|---|
| 2nd DNA SEGMENT | 5' | C | B | A | I | | 3' |
| 1st OLIGO. PRIMER | 3' | | | a' | i' | p' | 5' |

10. REVERSE TRANSCRIPTASE + dNTP's

| | | | | | | | |
|---|---|---|---|---|---|---|---|
| 2nd DNA SEGMENT | 5' | C | B | A | I | P | 3' |
| 1st DNA SEGMENT | 3' | c' | b' | a' | i' | p' | 5' |

11. T7 RNA POLYMERASE + NTP's

| | | | | | | |
|---|---|---|---|---|---|---|
| RNA PRODUCT | 3' | c' | b' | a' | i' | | 5' |

FIG. 1C

| | | | | | | | |
|---|---|---|---|---|---|---|---|
| NATURAL DNA TARGET: 1 | 5' | nnn | C | B | A | nnnnnnnnnn | 3' |
| NATURAL DNA TARGET: 2 | 3' | nnn | c' | b' | a' | nnnnnnnnnn | 5' |

1. RESTRICTION ENZYME

| | | | | | | |
|---|---|---|---|---|---|---|
| NATURAL DNA TARGET: 1 | 5' | nnn | C | B | A | 3' |
| NATURAL DNA TARGET: 2 | 3' | nnn | c' | b' | a' | 5' |

2. DENATURE

| | | | | | | |
|---|---|---|---|---|---|---|
| NATURAL DNA TARGET: 1 | 5' | nnn | C | B | A | 3' |
| | | | | + | | |
| NATURAL DNA TARGET: 2 | 3' | nnn | c' | b' | a' | 5' |

3. PRIMING

| | | | | | | | | |
|---|---|---|---|---|---|---|---|---|
| NATURAL DNA TARGET: 1 | 5' | nnn | C | B | A | | | 3' |
| 1st OLIGO. PRIMER | 3' | | | | a' | i' | p' | 5' |

4. REVERSE TRANSCRIPTASE + dNTP's

| | | | | | | | | |
|---|---|---|---|---|---|---|---|---|
| NATURAL DNA TARGET: 1 | 5' | nnn | C | B | A | I | P | 3' |
| 1st DNA SEGMENT | 3' | nnn | c' | b' | a' | i' | p' | 5' |

5. T7 RNA POLYMERASE + NTP's

| | | | | | | |
|---|---|---|---|---|---|---|
| RNA PRODUCT | 3' | c' | b' | a' | i' | 5' |

6. PRIMING

| | | | | | | |
|---|---|---|---|---|---|---|
| 2nd OLIGO. PRIMER | 5' | C | | | | 3' |
| RNA PRODUCT | 3' | c' | b' | a' | i' | 5' |

7. REVERSE TRANSCRIPTASE + dNTP's

| | | | | | | |
|---|---|---|---|---|---|---|
| 2nd DNA SEGMENT | 5' | C | B | A | I | 3' |
| RNA PRODUCT | 3' | c' | b' | a' | i' | 5' |

8. RIBONUCLEASE H

| | | | | | | | |
|---|---|---|---|---|---|---|---|
| 2nd DNA SEGMENT | 5' | C | B | A | I | P | 3' |

9. PRIMING

| | | | | | | | | |
|---|---|---|---|---|---|---|---|---|
| 2nd DNA SEGMENT | 5' | C | B | A | I | | | 3' |
| 1st OLIGO. PRIMER | 3' | | | | a' | i' | p' | 5' |

10. REVERSE TRANSCRIPTASE + dNTP's

| | | | | | | | |
|---|---|---|---|---|---|---|---|
| 2nd DNA SEGMENT | 5' | C | B | A | I | P | 3' |
| 1st DNA SEGMENT | 3' | c' | b' | a' | i' | p' | 5' |

11. T7 RNA POLYMERASE + NTP's

| | | | | | | |
|---|---|---|---|---|---|---|
| RNA PRODUCT | 3' | c' | b' | a' | i' | 5' |

FIG. ID

| | | | | | | | |
|---|---|---|---|---|---|---|---|
| NATURAL DNA TARGET:1 | 5' | nnn | C | B | A | nnnnnnnnnn | 3' |
| NATURAL DNA TARGET:2 | 3' | nnn | c' | b' | a' | nnnnnnnnnn | 5' |

1. DENATURE

| | | | | | | | |
|---|---|---|---|---|---|---|---|
| NATURAL DNA TARGET:1 | 5' | nnn | C | B | A | nnnnnnnnnn | 3' |
| | | | | + | | | |
| NATURAL DNA TARGET:2 | 3' | nnn | c' | b' | a' | nnnnnnnnnn | 5' |

2. PRIMING

| | | | | | | | | |
|---|---|---|---|---|---|---|---|---|
| NATURAL DNA TARGET:1 | 5' | nnn | C | B | A | nnnnnnnnnn | | 3' |
| 1st OLIGO. PRIMER | 3' | | | | a' | i' | p' | 5' |

3. REVERSE TRANSCRIPTASE + dNTP's

| | | | | | | | | |
|---|---|---|---|---|---|---|---|---|
| NATURAL DNA TARGET:1 | 5' | nnn | C | B | A | nnnnnnnnnn | | 3' |
| 1st DNA SEGMENT | 3' | nnn | c' | b' | a' | i' | p' | 5' |

4. DENATURE

| | | | | | | | | |
|---|---|---|---|---|---|---|---|---|
| NATURAL DNA TARGET:1 | 5' | nnn | C | B | A | nnnnnnnnnn | | 3' |
| | | | | + | | | | |
| 1st DNA SEGMENT | 3' | nnn | c' | b' | a' | i' | p' | 5' |

5. PRIMING

| | | | | | | | | |
|---|---|---|---|---|---|---|---|---|
| 2nd OLIGO. PRIMER | 5' | | C | | | | | 3' |
| 1st DNA SEGMENT | 3' | nnn | c' | b' | a' | i' | p' | 5' |

6. REVERSE TRANSCRIPTASE + dNTP's

| | | | | | | | | |
|---|---|---|---|---|---|---|---|---|
| 2nd DNA SEGMENT | 5' | | C | B | A | I | P | 3' |
| 1st DNA SEGMENT | 3' | nnn | c' | b' | a' | i' | p' | 5' |

7. T7 RNA POLYMERASE + NTP's

| | | | | | | |
|---|---|---|---|---|---|---|
| RNA PRODUCT | 3' | c' | b' | a' | i' | 5' |

8. PRIMING

| | | | | | | |
|---|---|---|---|---|---|---|
| 2nd OLIGO. PRIMER | 5' | C | | | | 3' |
| RNA PRODUCT | 3' | c' | b' | a' | i' | 5' |

9. REVERSE TRANSCRIPTASE + dNTP's

| | | | | | | |
|---|---|---|---|---|---|---|
| 2nd DNA SEGMENT | 5' | C | B | A | I | 3' |
| RNA PRODUCT | 3' | c' | b' | a' | i' | 5' |

10. RIBONUCLEASE H

| | | | | | | |
|---|---|---|---|---|---|---|
| 2nd DNA SEGMENT | 5' | C | B | A | I | P | 3' |

11. PRIMING

| | | | | | | | |
|---|---|---|---|---|---|---|---|
| 2nd DNA SEGMENT | 5' | C | B | A | I | | 3' |
| 1st OLIGO. PRIMER | 3' | | | a' | i' | p' | 5' |

12. REVERSE TRANSCRIPTASE + dNTP's

| | | | | | | | |
|---|---|---|---|---|---|---|---|
| 2nd DNA SEGMENT | 5' | C | B | A | I | P | 3' |
| 1st DNA SEGMENT | 3' | c' | b' | a' | i' | p' | 5' |

13. T7 RNA POLYMERASE + NTP's

| | | | | | | |
|---|---|---|---|---|---|---|
| RNA PRODUCT | 3' | c' | b' | a' | i' | 5' |

ENHANCED NUCLEIC ACID AMPLIFICATION PROCESS

This application is a continuation-in-part of application Ser. No. 07/211,384, filed Jun. 24, 1988.

FIELD OF THE INVENTION

This invention relates to an enhanced process for amplifying a specific nucleic acid sequence.

BACKGROUND OF THE INVENTION

The detection of a specific nucleic acid sequence present in a sample by probing the sample with a complementary sequence of nucleic acids is a known diagnostic technique. Nucleic acids are highly specific in binding to complementary nucleic acids and are thus useful to determine whether a specific nucleic acid is present in a sample. One must know the sequence of the specific nucleic acid to be detected and then construct a probe having a complementary nucleic acid sequence to the specific nucleic acid sequence.

In this application, the phrase "specific nucleic acid sequence" means a single stranded or double stranded nucleic acid which one wishes to amplify; "sample" means a mixture containing nucleic acids; "sufficiently complementary" means that two nucleic acids, a primer and a template, are capable of specific interaction which allows efficient, primer-dependent and template-directed synthesis of DNA, under given conditions of ionic strength and temperature. "DMSO" means dimethyl sulfoxide of sufficient purity to be used in molecular genetic reactions without any ill-effects on substrates or enzymes used. "BSA" means bovine serum albumin of a quality suitable for use in molecular biologic reactions and, in this regard, should be free from any DNases, DNA nicking activity, RNases and proteases.

Since nucleic acid probes are highly specific, it is preferable in some situations to probe the nucleic acid sequence itself rather than the protein produced by the nucleic acid sequence. As a particular example, a diagnostic method based solely on protein detection would be unreliable for determining the presence of infectious Particles of hepatitis B virus, due to the presence of significant levels of non-infectious antigen particles which lack the DNA genome. In another example, the various subtypes of human papilloma virus found in either pre-cancerous or benign cervical tumors can be distinguished only by the use of nucleic acid probe hybridization. Also, the specific genetic makeup of an AIDS virus makes it certain that an assay based on the presence of an AIDS virus specific nucleic acid sequence would be superior as a diagnostic.

The greatest difficulty and limitation with applying existing nucleic acid probe technology, is the copy number problem. In a virus or cell, for example, there is usually a single copy of a particular gene. This one copy may give rise to many copies of gene product, either RNA or protein. For this reason, diagnostic techniques have often involved probing the protein, since the specific sequence of nucleic acid to be detected may give rise to many thousand copies of protein.

The naturally-occurring high number of ribosomal RNA, up to 100,000 copies per cell, has been used by GenProbe to facilitate diagnosis of certain bacterial pathogens, such as Legionella and Mycoplasma, using nucleic acid probes. However, this strategy cannot be used with non-cellular pathogens, such as viruses, or with probed nucleic acid sequences with low copy numbers. Copy number is a particular problem with the development of a nucleic acid probe method for the detection of AIDS virus, where the integrated provirus may be present in less than one of ten thousand peripheral blood lymphocytes. Thus, if the particular nucleic acid sequence suspected to be present in a sample could be amplified, the copy number problem could be circumvented and probe assays could be more readily used.

In a normal biological sample, containing only a few cells, and consequently only a few copies of a particular gene, it is necessary to utilize an amplification process in order to overcome the copy number problem.

One method to amplify is to 'grow out' the sample, that is, to arrange conditions so that the living biological material present in the sample can replicate itself. Replication could increase the quantity of nucleic acid sequences to detectable levels. In the food industry, for example, in order to test processed food for the food-poisoning bacteria Salmonella, food samples must be incubated for a number of days to increase the quantity of nucleic acid copy numbers. In clinical samples, pathogens must also be allowed to increase their number by growing out over some considerable time.

U.S. Pat. No. 4,683,195 issued Jul. 28, 1987 to Cetus Corporation and U.S. Pat. No. 4,683,202 issued on Jul. 28, 1987 to Cetus Corporation are each directed to a process for amplifying a target nucleic acid sequence contained in a sample. U.S. Pat. No. 4,683,195 relates to a process in which a sample suspected of containing a target DNA sequence is treated with oligonucleotide primers such that a primer extension product is synthesized which in turn serves as a template, resulting in amplification of the target a DNA sequence. The primer extension product is separated from the template in the preferred embodiment using heat denaturation. Similarly, U.S. Pat. No. 4,683,202 relates to a process for amplifying a target DNA sequence having two separate complementary strands. The process includes treating the strands with primers to synthesize extension products, separating the primer extension products from the templates, and in turn using the primer extension products as templates.

Both of the above United States patents require either manual or mechanical participation and multi-step operations by the user in the amplification process and are restricted to amplifying DNA only. The steps involved in these patents require the user to heat the sample, cool the sample, add appropriate enzymes and then repeat the steps. The temperature changes cause the enzymes to loose their activity. Hence, the user is required to repeatedly supplement the amplification mixture with aliquots of appropriate enzymes during the amplification process.

In addition, in U.S. Pat. Nos. 4,683,195 and 4,683,202 each cycle of the amplification process takes place by the synthesis from a first template, of a second template, the second template in turn is used to synthesize the first template. This procedure is repeated, thus, each cycle of the amplification process is based on the synthesis of one product from one substrate.

Notwithstanding the amplification processes disclosed in the prior art, a need exists for improvements to the amplification process. It would be preferable if the amplification process required less participation and fewer manipulations by the user and not be restricted to DNA. Further, it would be advantageous if the amplification took place at a relatively constant ambient temperature so that the activity of the enzymes involved in the process would not be affected. It would be more expedient if a template could be used to generate more than one product from one substrate in each cycle of the amplification process.

SUMMARY OF THE INVENTION

This invention relates to an amplification process of single stranded RNA (ssRNA), single-stranded DNA (ssDNA) or double-stranded DNA (dsDNA) which is expedient and requires less participation and fewer manipulations by the user of the process than conventional amplification processes. The amplification takes place at a relatively constant ambient temperature. In addition, each cycle of the process generates a plurality of copies of product from one antisense RNA template. The amplification process of this invention may be used to increase the quantity of a specific nucleic acid thus circumventing the copy number problem. Hence, probe assays may be more readily used. The amplification process could also be used to increase the purity of a specific nucleic acid sequence as a substitute for conventional cloning methodology.

According to one aspect of the invention, a process for amplifying a specific nucleic acid sequence is used. The process involves the synthesis of single-stranded RNA, single-stranded DNA, and double stranded DNA. The single stranded antisense RNA is a first template for a second primer. The single stranded DNA is a second template for a first primer. The double stranded DNA is a third template for the synthesis of a plurality of copies of the first template. A sequence of the first or the second primer is sufficiently complementary to a sequence of the specific nucleic acid sequence and a sequence of the first or the second primer is sufficiently homologous to a sequence of the specific nucleic acid sequence. A second primer binds to the 3' end of the first RNA template and generates the second DNA template. A 3' end of the first primer hybridizes to the 3' end of the second DNA template. The second template is removed from the first template and is used to generate a complementary DNA strand. The resulting duplex DNA serves as a third template for synthesizing a plurality of first templates which in turn repeat the above-described cycle.

According to another aspect of the invention, a process for amplifying a specific nucleic acid sequence is used. The process involves:

(a) hybridizing a first primer to a first template. The first primer has a DNA sequence which is sufficiently complementary to a RNA sequence of the first template;

(b) synthesizing a first DNA sequence covalently attached to the first primer and complementary to the RNA sequence of the first template. The first DNA sequence and the first primer comprise a second template;

(c) separating the first template from the second template to allow hybridization of a second primer;

(d) hybridizing the second primer to the second template. The second primer has a DNA sequence which is sufficiently complementary to a DNA sequence of the second template. The second primer also has a complementary sequence of a promoter and a complementary sequence of a transcription initiation site for a RNA polymerase;

(e) synthesizing a second DNA sequence covalently attached to the second primer and complementary to the DNA sequence of the second template and synthesizing a third DNA sequence covalently attached to the second template and complementary to the DNA sequence of the second primer. The second and third DNA sequences, the second primer and the second template comprise a third template;

(f) synthesizing a plurality of copies of the RNA sequence of the first template from the third template.

Alternatively the amplification process according to the present invention involves the following steps. Step (A) provides a single reaction medium containing a first oligodeoxynucleotide primer, the first primer comprising a sequence that is a functional promoter; a second oligodeoxynucleotide primer, the second primer comprising a 5' end segment complementary to a functional promotor; an RNA-directed DNA polymerase; a DNA-directed DNA polymerase; a DNA-directed RNA polymerase; a ribonuclease that removes RNA of an RNA/DNA hybrid without hydrolyzing single- or double-stranded RNA or DNA; ribonucleoside and deoxyribonucleoside triphosphates; and at least one of DMSO or BSA. Step (B) provides for adding to the reaction medium one or more of the following (i) a single-stranded RNA molecule comprising (a) a sense RNA sequence that hybridizes at its 3' end to a portion of the 3' end of the second primer; or (b) an anti-sense RNA sequence that is hybridized at its 3, end by the first primer, (ii) a single-stranded DNA molecule comprising (a) a second-primer binding DNA sequence that hybridizes at its 3' end to the 3' end of the second primer; or (b) a promotor-complementary DNA sequence that comprises a 5'-end sequence complementary to a functional promoter; or (c) a first-primer binding DNA sequence that is hybridized at its 5' end by the first primer, (iii) a denatured double-stranded DNA molecule comprising an amplifiable segment and a functional promoter, the functional promotor being adjacent to the segment and oriented to control transcription of the segment. Step (C) provides for establishing conditions such that at least one of the group consisting of a portion of the RNA molecule, the single-stranded DNA molecule and the double-stranded DNA molecule is used as a template for generating one or more copies of the anti-sense RNA sequence and wherein the anti-sense RNA sequence initiates a cycle in the reaction medium comprising the steps of:(i)hybridizing the first primer to a region at the 3' end of the anti-sense RNA sequence; (ii) forming an RNA/DNA hybrid by action of the RNA-directed DNA polymerase, the RNA/DNA hybrid comprising a first DNA segment covalently attached to the 3' end of the first primer to form a second DNA segment, the first DNA segment being complementary to at least a portion of the anti-sense RNA sequence; (iii) releasing the second DNA segment from the RNA/DNA hybrid by action of the ribonuclease on at least some portion of the anti-sense RNA sequence; (iv) hybridizing the 3' end of the second DNA segment with the 3' end of the second primer to form a duplex that is acted upon by the DNA-directed DNA polymerase to produce (a) a third DNA segment which is covalently attached to the 3' end of the second primer and which is complementary to the first DNA segment, and (b) a fourth DNA segment comprising the third DNA segment and the first primer, and (c) a fifth DNA segment which is covalently attached to the 3' end of the second DNA segment and which is complementary to the nonduplexed 5' end of the second primer, and (d) a sixth DNA segment comprising the second DNA segment and the fifth DNA segment; and (v) producing (a) a plurality of RNA sequences corresponding to the antisense RNA sequence by action of the RNA polymerase on the duplex and (b) a plurality of DNA sequences corresponding to the fourth DNA segment and to the sixth DNA segment.

A sequence of the first or the second primer is sufficiently complementary to a sequence of the specific nucleic acid sequence and a sequence of the first or the second primer is sufficiently homologous to a sequence of the specific nucleic acid sequence. A 3' end of the first primer is oriented towards a 3' end of the second primer on complementary strands.

In a further alternative of the invention, the second primer of DNA has a sequence at its 3' end which is sufficiently complementary to the DNA sequence of the second template. The second primer has at its 5' end a complementary sequence of a promoter and a complementary sequence of a transcription initiation site for a RNA polymerase.

In a further alternative of the invention, the third DNA sequence covalently attached to the second template is complementary to the DNA sequence at the 5' end of the second primer.

In another alternative of the invention, a process for amplifying a specific nucleic acid sequence is used. The process involves combining a first primer, a second primer, ribonuclease H, a RNA-directed DNA polymerase, a DNA-directed DNA polymerase, a RNA polymerase, ribonucleoside triphosphates and deoxyribonucleotide triphosphates with a sample. The first primer of DNA has a sequence which is sufficiently complementary to a first template of RNA. The second primer of DNA has a sequence which is sufficiently complementary to a second template of DNA, and a complementary sequence of a promoter and a complementary sequence of a transcription initiation site which are recognized as substrate by the RNA polymerase. A sequence of the first primer or the second primer is sufficiently complementary to a sequence of the specific nucleic acid sequence and a sequence of the first primer or the second primer is sufficiently homologous to a sequence of the specific nucleic acid. A 3' end of the first primer is oriented towards a 3' end of the second primer on complementary strands.

In a further alternative of the invention, a process for amplifying a specific nucleic acid sequence is used. The process involves adding a first primer, a second primer, avian myelooblastosis viral polymerase, E. coli ribonuclease H, bacteriophage T7 RNA polymerase, ribonucleoside triphosphates and deoxyribonucleotide triphosphates to a sample. The first primer of DNA has a sequence which is sufficiently complementary to a first template of RNA. The second primer of DNA has a sequence which is sufficiently complementary to a second template of DNA, and a complementary sequence of a promoter and a complementary sequence of a transcription initiation site which are recognized as substrate by T7 RNA polymerase. A sequence of the first primer or the second primer is sufficiently complementary to a sequence of the specific nucleic acid sequence and a sequence of the first primer or the second primer is sufficiently homologous to a sequence of the specific nucleic acid sequence. A 3' end of the first primer is oriented towards a 3' end of the second primer on complementary strands.

Another aspect of the present invention provides for a kit for amplifying nucleic acid molecules, comprising an assemblage of (a) a receptacle containing a solution of a first oligonucleotide primer, (b) a receptacle containing a solution of a second oligonucleotide primer, (c) a receptacle containing a solution of a ribonuclease that hydrolyses RNA of an RNA/DNA hybrid without attacking single- or double-stranded RNA or DNA, (d) a receptacle containing a solution of an RNA-directed DNA polymerase,(e) a receptacle containing a solution of a DNA-directed RNA polymerase, (f) a receptacle containing a solution of a DNA directed DNA polymerase, (g) a receptacle containing a solution of ribonucleoside triphosphates, (h) a receptacle containing a solution of deoxyribonucleotide triphosphates, (i) a receptacle containing a solution of DMSO, and (j) a receptacle containing a solution of BSA.

According to another aspect of the present invention, a nucleic acid amplification process is provided wherein the DMSO is provided at a concentration in the in the range from 0-30% and the BSA is provided at a concentration in the range of 5-2500 $\mu$g/ml. Alternatively, the DMSO is provided at a concentration in the in the range from 0%-30% and the BSA is provided at a concentration in the range of 50-500 $\mu$g/ml. Additionally, the DMSO is provided at a concentration in the in the range from 15-25% and the BSA is provided at a concentration in the range of 50-500 $\mu$g/ml.

According to another aspect of the present invention, the amplification with DMSO and BSA is increased over the amplification without added DMSO or BSA at least 10 fold. In another aspect, the amplification is increased over the amplification without added DMSO or BSA at least 1000 fold. In still another aspect of the present invention, the amplification is increased over the amplification without added DMSO or BSA at least $10^4$ fold. In another aspect of the present invention, the amplification is increased over the amplification without added DMSO or BSA at least $10^6$ fold. In still another aspect of the present invention, the amplification is increased over the amplification without added DMSO or BSA at least $10^8$ fold.

BRIEF DESCRIPTION OF THE DRAWINGS

In drawings which illustrate embodiments of the invention,

FIG. 1b is an example of the nucleic acid amplification process starting with a sense (+) RNA molecule.

FIG. 1c is an example of the nucleic acid amplification process starting with a dsDNA that has been cut with a restriction endonuclease and then denatured.

FIG. 1d is an example of the nucleic acid amplification process starting with a dsDNA that has been denatured.

FIG. 2 shows the synthetic oligonucleotides DNA sequences which are used for testing the amplification process.

DETAILED DESCRIPTION OF THE PREFERRED EMBODIMENTS

Figure 1A:
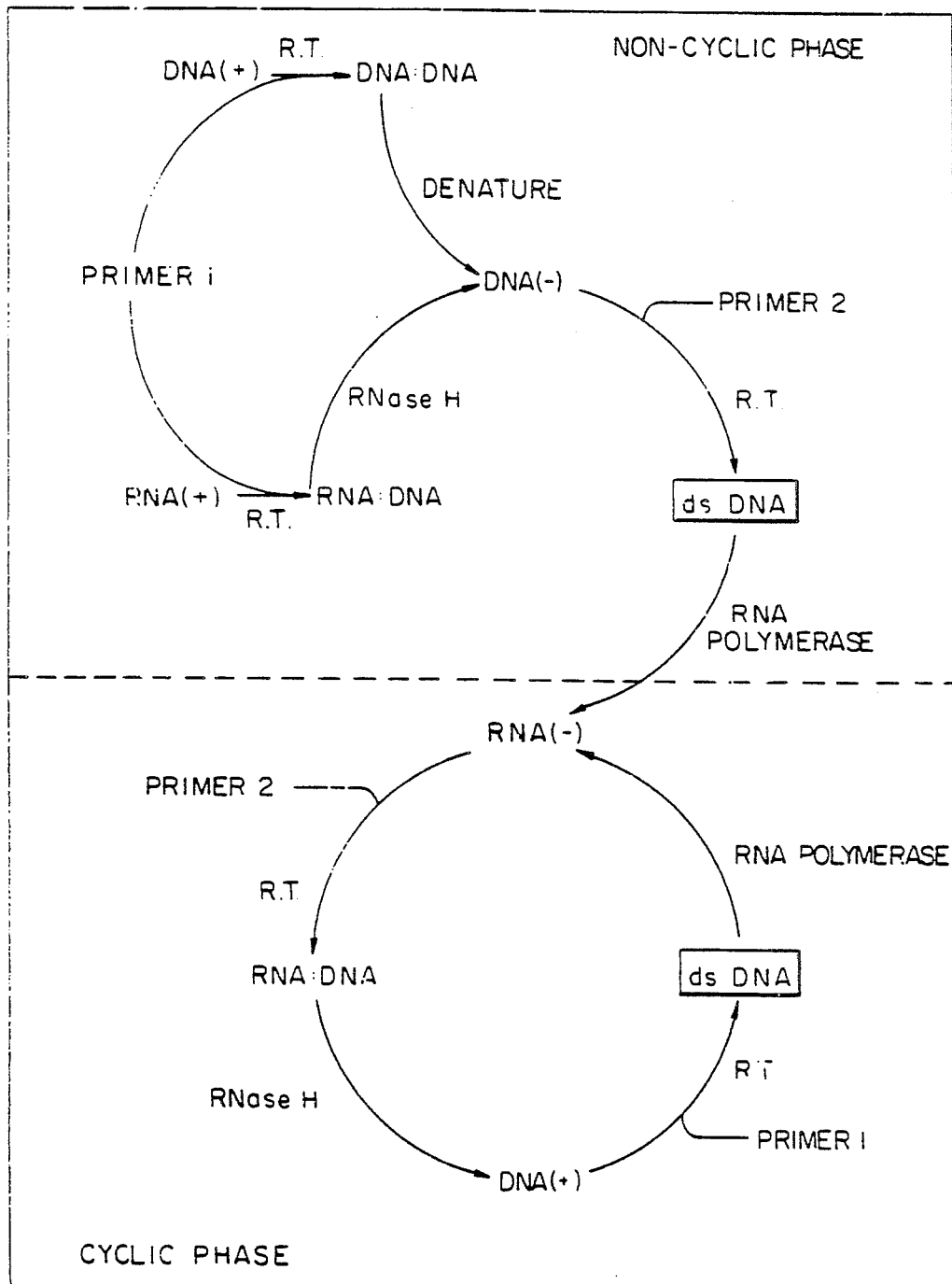
FIG. 1a is a general illustration of the nucleic acid amplification process.

This invention relates to a process for amplifying a specific nucleic acid sequence. The amplification involves the alternate synthesis of DNA and RNA and is generally and specifically illustrated in FIGS. 1a–1d. In this process, single-stranded antisense (−) RNA is converted to single-stranded DNA which in turn is converted to dsDNA and becomes a functional template for the synthesis of a plurality of copies of the original single-stranded RNA. A first primer and a second primer are used in the amplification process. A sequence of the first primer or the second primer is sufficiently complementary to a sequence of the specific nucleic acid sequence and a sequence of the first or the second primer is sufficiently homologous to a sequence of the specific nucleic acid sequence. In some instances, both the first primer and second primer are sufficiently complementary and sufficiently homologous to a sequence of the specific nucleic acid sequence, for example, if the specific nucleic acid sequence is double stranded DNA.

The (−) RNA is converted to single-stranded DNA by hybridizing an oligonucleotide primer (the first primer) to 3' end of the RNA (the first template) and synthesizing a complementary strand of DNA from the first primer (the first DNA sequence) by using a RNA-directed DNA polymerase. The resulting single-stranded DNA (the second template) is separated from the first template by, for example, hydrolysis of the first template by using a ribonuclease which is specific for RNA-DNA hybrids (for example, ribonuclease H). The second template is converted to a form which is capable of RNA synthesis by hybridizing a synthetic oligonucleotide (the second primer), which contains at its 3' end a sequence which is sufficiently complementary to the 3' end of the second template and toward its 5' end a sequence containing a complementary strand of a promoter and antisense sequence of a transcription initiation site, and by synthesizing a second DNA sequence covalently attached to the 3' end of the second primer using the second template as a template and synthesizing a third DNA sequence covalently attached to the 3' end of the second template using the second primer as a template, using DNA-directed DNA polymerase. The resulting functional derivative of the second template, which is a third template, is used for the synthesis of a plurality of copies of RNA, the first template, by using a RNA polymerase which is specific for the promoter and transcription initiation site defined by the second primer. Each newly synthesized first template can be converted to further copies of the second template and the third template by repeating the cycle. In addition, repetition of the cycle does not require participation or manipulation by the user.

The amplification process commences with the addition of a suitable template nucleic acid to the appropriate enzymes, primers, and cofactors under the appropriate reaction conditions. This template nucleic acid is in a form which is capable of homogenous and continuous amplification and can function as an intermediate in the cycle set forth in FIG. 1a. The amplification process involves the net consumption of precursors (primers, ribonucleoside triphosphates and deoxyribonucleotide triphosphates) and the net accumulation of products (RNA and DNA). The processes of RNA and DNA synthesis will proceed asynchronously until sufficient levels of nucleic acids have been synthesized to allow detection. The amplification process may be monitored by, for example, the synthesis of a labeled product from a labeled precursor.

It is contemplated that amplification may involve another process either in addition to or in place of the one generally illustrated in FIG. 1a. Also possible are certain counter-productive enzymatic reactions which occur at permissibly low rates. Included among the possible non-productive side reactions is the synthesis of RNA and/or DNA in the absence of an added template nucleic acid. Such RNA and/or DNA products can be discriminated from desired products by determining whether a particular sequence which would be found only between the two priming sites of the specific nucleic acid sequence is present.

The first primer is an oligodeoxyribonucleotide which has at its 3' end a sequence which is sufficiently complementary to the 3' end of the first template. The sequence at the 3' end of the first primer has a particular length and base composition to allow specific and efficient synthesis of the first DNA sequence, under the given conditions of ionic strength and temperature. The first primer may be sufficiently complementary to a region internal to the 3' end of the first template in the first cycle In subsequent cycles, the 5' end of the first primer would be complementary to the 3' end of the first template. It is contemplated that the first primer may be composed partially or completely of nucleotides or nucleotide analogs other than the natural deoxyribonucleotides. The 5' end of the first primer may contain sequences which are not complementary to the first template in the first cycle. The non-complementary sequences may be complementary to a nucleic acid which can be immobilized, or to which can be bound a useful non-nucleic acid component, such as a reporter to facilitate detection. Alternatively, the non-complementary sequences may include a complementary sequence of a promoter and a complementary sequence of a transcription initiation site, which could be used for the synthesis of RNA. This RNA would be complementary to the first template and could be used as an intermediate in another amplification cycle.

The second primer is an oligodeoxyribonucleotide which contains at its 3' end a sequence which is sufficiently complementary to the 3' end of the second template. The second primer has a particular length and base composition to allow specific and efficient synthesis of the second and third DNA sequences, under the given conditions of ionic strength and temperature. In addition, the second primer contains the antisense sequence of a functional promoter and the antisense sequence of a transcription initiation site. This sequence, when used as a template for synthesis of the third DNA sequence, contains sufficient information to allow specific and efficient binding of a RNA polymerase and initiation of transcription at the desired site. The promoter sequence may be derived from the antisense strand of a functional promoter. The transcription initiation site may be derived from the 5' terminal sequence of a natural RNA transcript. In a preferred embodiment, the 5'-terminal sequence of the second primer is AATTCTAATACGACTCACTATAGGGAG. This sequence contains the antisense sequence of the promoter and the antisense sequence of the transcription initiation site for T7 RNA polymerase. Alternatively, the transcription initiation site and Promoter for another phage RNA polymerase may be used. In addition, sequences which are unrelated to the promoter function may be included at the 5' end of the second primer or between the transcription initiation site and the sequence at the 3' end which hybridizes to the second template. It is contemplated that the second primer may be composed partially or completely of nucleotides or nucleotide analogs other than natural deoxyribonucleotides.

All of the enzymes used in this invention should meet certain practical specifications. Each enzyme or enzyme preparation should be free of deleterious deoxyribonuclease ("DNase") activities, such as the 5' or 3' exonuclease activities which are often associated with certain DNA polymerases and single-strand or double-strand specific exonuclease or endonucleases. Each enzyme or enzyme preparation should be free of deleterious ribonuclease ("RNase") activities, with the exception of the preferred addition of a ribonuclease activity which is specific for hybrids of RNA and DNA (for example, ribonuclease H). In addition, each enzyme should be reasonably active under the common reaction conditions which are used for the other enzymatic processes, and non-enzymatic processes, such as hybridizing oligonucleotide primers to the RNA or DNA templates.

The DNA-directed RNA polymerase which is used in this invention may be any enzyme capable of binding to a particular DNA sequence called a promoter and specifically initiating in vitro RNA synthesis at a defined initiation site within close proximity to the promoter. The promoter and the initiation site form part of the second primer. In addition the RNA polymerase should be capable of synthesizing several copies of RNA per functional copy of template in a reasonable amount of time. In the preferred embodiment, the bacteriophage T7 RNA polymerase is used. In addition other bacteriophage RNA polymerases, such as phage T3, phage φII, Salmonella phage sp6, or Pseudomonas phage gh-1 may be used. In another embodiment, other prokaryotic or eukaryotic DNA-directed RNA polymerase may be used. It should be understood that if alternative RNA polymerases are used, then the necessary changes to the promoter and initiation sequences of the second primer should be made according to the template specificity of the particular RNA polymerase.

The RNA-directed DNA polymerase which is used in this invention may be any enzyme capable of synthesizing DNA from an oligodeoxyribonucleotide primer and a RNA template. In addition this enzyme may contain activities for DNA-directed DNA polymerase and RNase H. In the preferred embodiment, the avian myelooblastosis viral polymerase ("AMV reverse transcriptase") is used. In addition, the RNA-directed DNA polymerase could be from another retrovirus, such as Moloney murine leukemia virus. Alternatively, other eukaryotic RNA-directed DNA polymerases could be used.

The DNA-directed DNA polymerase which is used in this invention may be any enzyme capable of synthesizing DNA from an oligodeoxyribonucleotide primer and a DNA template. This enzyme should not contain either 5'- or 3'- exonuclease activities, which are associated with many types of DNA polymerase. In the preferred embodiment, the AMV reverse transcriptase is used. However, other DNA-directed DNA polymerases which naturally lack the 5'-or 3.- exonuclease activities could be used. These could include certain eukaryotic DNA polymerases, such as, DNA polymerase or β those DNA polymerases which could be isolated from a mammalian tissue, such as calf thymus. An otherwise unsuitable DNA polymerase could be made useful by removing the undesirable exonuclease activities either by alteration of the DNA polymerase gene followed by expression of the altered polymerase in a suitable host cell, or by chemical modification of the DNA polymerase protein. Altered versions of DNA polymerase could be made from the Klenow fragment of E. coli DNA polymerase I or the bacteriophage T7 DNA polymerase. It should be understood that such alternative DNA-directed DNA polymerase activities are added to supplement the activity contributed by the RNA-directed DNA polymerase, since in the preferred embodiment, both RNA-directed and DNA-directed DNA polymerase activities are supplied by the same enzyme.

The RNase H which could be used in this invention may be any enzyme capable of hydrolyzing a RNA which is annealed to a complementary DNA. This enzyme should not be capable of hydrolyzing single or double-stranded RNA or any DNA. In the preferred embodiment, the E. coli RNase H is used. In addition, other RNase H enzymes could be used, such as calf thymus RNase H. Since RNase H is an intrinsic activity of AMV reverse transcriptase, the E. coli RNase H will be supplemented in the preferred embodiment by the RNase H of AMV reverse transcriptase. Alternatively, any other enzyme capable of separating the second template from the first template could be used.

The above-mentioned enzymes and primers are mixed together in a reaction vessel which contains the necessary buffers and cofactors for both DNA and RNA synthesis. In addition, the ionic conditions and reaction temperature should be compatible with specific hybridization of the primers to the DNA and RNA templates as is known to those skilled in the art. The reaction mixture should be free of such agents which would interfere with the amplification process, specifically substances which could greatly inhibit the activity of the enzymes, interfere with the hybridizing of primers and templates, or degrade non-productively the nucleic acid intermediates and products.

The description of possible detection schemes may be useful to the application of the amplification process. It should be understood that schemes which may be used for detecting the nucleic acids which are synthesized in the amplification process are not limited to those described herein, and it is contemplated that other methods may be used.

In one embodiment, a labeled precursor may be added to the reaction mixture. Amplification is determined by quantitative or qualitative analysis of labeled products, which can be separated from the labeled precursor by using methods known in the art. A labeled precursor may be a ribonucleoside triphosphate for detecting RNA synthesis, or a deoxynucleoside triphosphate or an oligonucleotide primer for detecting DNA synthesis. The type of label may be a radioisotope or a useful chemical group, such as biotin, a chromophobe, a fluorophore, or a hapten which could bind to an antibody, or possibly a protein or an enzyme. The labeled products may be separated from the labeled precursors on the basis of solubility, charge, or size. In addition, the labeled DNA or RNA may be hybridized to a nucleic acid which contains a complementary sequence and which can be immobilized.

In another embodiment, the products of the amplification process may be bound to an immobilized support, hybridized to a nucleic acid probe containing a complementary sequence, and separated from the unhybridized nucleic acid probe which remains in solution. The products, DNA or RNA, may be bound directly to a solid support by any stable interaction, such as hydrophobic, electrostatic, or covalent interaction. In addition, the Products may contain certain chemical groups, for example, biotin, which may be incorporated into the products during the amplification process to allow binding to an immobilized protein, for example, avidin or streptavidin. In addition, the products may be hybridized to a nucleic acid which contains a complementary sequence and which can be immobilized. The nucleic acid probe would contain a complementary sequence which forms a sufficiently stable interaction with a product of the amplification process to allow binding under the conditions of hybridization and sustained binding under the conditions used for removal of the unhybridized nucleic acid probe. In the preferred embodiment the complementary sequence would be derived from that part of the specific nucleic acid sequence which is between the sequences of the first primer and the second primer. The nucleic acid probe may be a single-stranded DNA or RNA, or a double-stranded DNA or RNA which can be made single-stranded, or an oligonucleotide which can be composed of deoxyribonucleotides and/or ribonucleotides. In addition, the nucleic acid probe may contain a chemical group which could covalently bind to a product DNA or RNA under the appropriate conditions. The nucleic acid probe may be labeled with a radioisotope or a useful chemical group, such as biotin, a chromophobe, a fluorophore, or a hapten which could bind to an antibody. In addition, the nucleic acid probe could be conjugated to a protein or enzyme, for example, a phosphatase or a peroxide. In addition, the nucleic acid probe may contain sequences which would allow in vitro replication of the probe.

It is contemplated that the products of the amplification process may be analyzed by methods which are typically used for nucleic acids that have been enriched by molecular cloning techniques. In one alternative, the synthesis of a specific DNA sequence may be detected by digestion of the synthesized DNA with a restriction endonuclease, followed by electrophoretic separation and detection using methods known in the art. In another alternative, the sequence of amplified RNA may be determined by DNA synthesis using a RNA-directed DNA Polymerase, the first primer, and dideoxynucleoside triphosphates (Stoflet et al., *Science* 239:491–494, 1988). In another alternative, the sequence of the amplified third template may be determined by RNA synthesis using the DNA-directed RNA polymerase used in the amplification process, and 3'-deoxyribonucleotide triphosphates (Axelrod & Kramer, *Biochem.* 24:5716–5723, 1985). In another alternative, the amplified RNA may encode a polypeptide which could be translated, in vitro. The polypeptide product of the in vitro translation could be analyzed by using an antibody.

A sample suspected of containing or known to contain the specific nucleic acid sequence is added to the reaction mixture in the form of a template nucleic acid which is capable of homogeneous and continuous amplification and may be any intermediate in the cycle set forth in FIG. 1. In particular, the template nucleic acid may be a single-stranded RNA which contains at its 5' end a sequence which is sufficiently homologous to that which is at the 3' end of the second primer, and contains a sequence which is sufficiently complementary to the first primer. A template nucleic acid of this form would function as a first template in the amplification process. Alternatively, the template nucleic acid may be a single-stranded DNA which contains at its 3. end a sequence which is sufficiently complementary to at least the 3' end of the second primer, and contains a sequence which is sufficiently homologous to that which is at the 3' end of the first primer. A template nucleic acid of this form would function as a second template in the amplification process. Alternatively, the template nucleic acid may be a double-stranded DNA, one strand of which contains at its 5 ' end the entire sequence of the second primer and contains a sequence which is sufficiently complementary to the first primer. The double-stranded DNA functions as a third template in the amplification process.

Although the preparation of a template nucleic acid is not part of the amplification process, the description of possible schemes for generating template nucleic acids may be useful to the application of the amplification process. It should be understood that the schemes which may be used for obtaining the template nucleic acid are not limited to the alternatives which are described herein, and it is contemplated that other methods may be used.

In one alternative, a template nucleic acid which could function as a first template could be a naturally occurring RNA or a RNA fragment which could be generated from a larger RNA molecule by using site specific hydrolysis methods known in the art (Shibahara et al., *Nucleic Acid Res.* 15:4403–4415, 1987).

In another alternative, a template nucleic acid which could function as a second template could be generated from a double-stranded DNA by digestion with a restriction endonuclease which has a site immediately flanking the sequence which is sufficiently complementary to the 3' end of the second primer. The resulting double-stranded DNA fragments could then be made single-stranded by using chemical or thermal denaturation methods.

In another alternative, a template nucleic acid which could function as a second template could be generated from a single-stranded DNA or RNA to which has been hybridized an oligonucleotide which is capable of blocking DNA synthesis. This blocking oligonucleotide may contain a chemical group, which could covalently bind to the template, under the appropriate conditions. DNA synthesis from this blocked template using the first primer could result in a synthesized DNA with the same 3' end as the second template. If the original template is RNA, then the resulting DNA-RNA hybrid may be used directly as a template nucleic acid. If the original template is DNA, then the resulting copy of the second template could then be separated from the original template by using chemical or thermal denaturation methods.

In another alternative, a template nucleic acid which could function as a third template could be generated from a single-stranded DNA or RNA by DNA synthesis from the DNA or RNA template using the second primer. The resulting synthesized DNA could then be separated from the original template by using chemical or thermal denaturation methods. In addition, a RNA template could be hydrolyzed by using chemical or enzymatic methods. The resulting single-stranded DNA has the sequence of the second primer covalently attached to its 5' end and contains a sequence which is sufficiently complementary to the first primer. This single-stranded DNA could be converted to a transcriptionally functional double-stranded DNA by hybridizing the first primer to the single-stranded DNA, and by synthesizing a DNA sequence which is convalently attached to the first primer and complementary to the single-stranded DNA.

In a further alternative, a single-stranded DNA or RNA template could be obtained from a double-stranded DNA, double-stranded RNA or a DNA-RNA hybrid by using chemical, thermal, or possibly enzymatic methods. Then, by using one of the alterative schemes proposed above, the resulting single-stranded DNA or RNA could then be used to generate a template nucleic acid which could function as a first, second or third template. In addition, an alternative scheme involving the first primer and one strand of nucleic acid, and another alternative scheme involving the second primer and the other (complementary) strand of the nucleic acid may be used concurrently to generate template nucleic acids.

It has been discovered, unexpectedly, that the addition of both DMSO and BSA to the reaction medium significantly increases the sensitivity and reproducibility of the above-descried amplification process. Target copy number in the range from 1 to $10^6$ are detectable and isolateable using the presently claimed invention. DMSO at final concentrations in the range between 0% and 30% and BSA at final concentrations in the range of from 5 $\mu$g/ml to 2500 $\mu$g/ml are useful for enhancing the sensitivity and reproducibility of the amplification process. In a preferred embodiment, a BSA concentration of the range from 50 $\mu$g/ml to 500 $\mu$g/ml and a DMSO concentration in the range from 15% to 25% are used. In another preferred embodiment, a BSA concentration of the range from 100 $\mu$g/ml to 300 $\mu$g/ml and a DMSO concentration in the range from 15% to 25% are used.

The use of DMSO and BSA in the amplification reaction medium provides enhanced sensitivity and reproducibility over the use of the reaction medium without DMSO and BSA, however the reaction medium alone is sufficient for the detection and isolation of targeted nucleic acid sequences. The use of DMSO and BSA in the reaction medium is suitable for increasing the amplification level at least 10 fold over that of the reaction medium alone. In a preferred embodiment the amplification using DMSO and BSA according to the presently claimed invention is increased by at least 100 fold. In another preferred embodiment the amplification using DMSO and BSA according to the presently claimed invention is increased by at least 1000 fold. In still another preferred embodiment the amplification using DMSO and BSA according to the presently claimed invention is increased by at least 10,000 fold. In another preferred embodiment the amplification using DMSO and BSA according to the presently claimed invention is increased by at least $10^6$ fold. In another preferred embodiment the amplification using DMSO and BSA according to the presently claimed invention is increased by at least $10^7$ fold. In another preferred embodiment the amplification using DMSO and BSA according to the presently claimed invention is increased by at least $10^8$ fold.

Alternatively, the use of other specific enhancement chemicals (SPCs) besides DMSO and BSA could be used according to the present invention that confer increases in amplification level over that of the reaction medium without SPCs.

Figure 3:
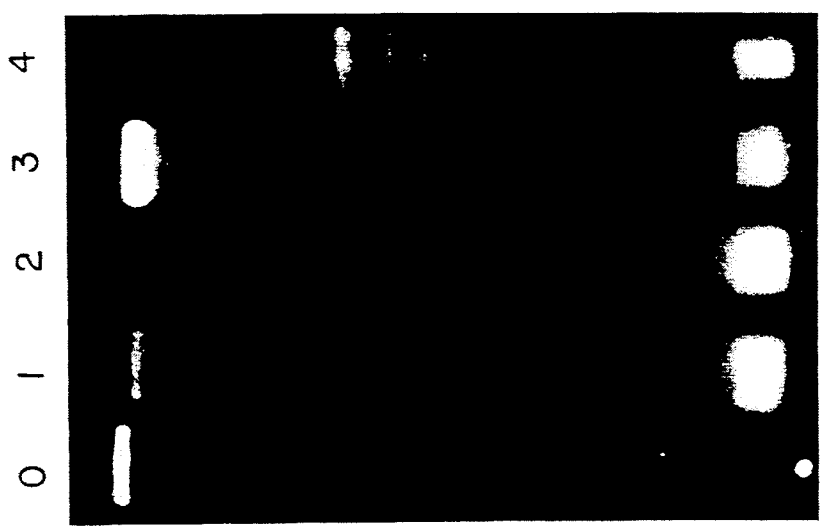
FIG. 3 is an autoradiogram of PAGE analysis of amplification reactions using different primer concentrations.

It has also been discovered, unexpectedly, that the addition of DMSO in the range of 2 to 20 percent to the reaction medium of the presently claimed amplification process has improved the reproducibility of the process, as demonstrated, for example, in FIG. 3. The use of DMSO alone, however, is also shown to decrease the amplification level starting between 15% and 20% DMSO in the reaction medium.

MATERIALS AND METHODS

Materials

Oligonucleotides were synthesized using an Applied Biosystems 380A DNA synthesizer. Columns, phosphoramidites, and reagents used for oligonucleotide synthesis were obtained from Applied Biosystems, Inc. through Technical Marketing Associates. Oligonucleotides were purified by polyacrylamide gel electrophoresis followed by DEAE cellulose chromatography. The radioisotope [−32 p] UTP (800 Ci/mmol) was from Amersham. Enzymes for digesting and ligating DNA were purchased from New England Biolabs, and used according to the supplier's recommendations. Preparations containing the large fragment of DNA polymerase 1 (Klenow) were also purchased from New England Biolabs. RNasin and T7 RNA polymerase from Promega Biotec were purchased through Bio/Can Scientific Inc. Reverse transcriptase and RNase H were obtained from Pharmacia. The supplier for proteinase K was Boehringer Mannheim Canada. *E. coli* strain HB101 (ATCC 33694) was used for all transformations. The plasmid pUC19 (Norrander et al., 1983) was purchased from Bethesda Research Laboratories.

Isolation of DNA and sequencing

*E. coli* transformants were grown on YT medium (Miller, EXPERIMENTS IN MOLECULAR GENETICS Cold Spring Harbor Laboratory, Cold Spring Harbor, N.Y., p. 433, 1972) containing 50 µg/ml ampicillin. Plasmid DNA was purified by a rapid boiling method (Holmes and Quigley, *Anal. Biochem.* 114:193–197, 1981). DNA fragments and vectors used for all constructions were separated by electrophoresis on low melting point agarose, and purified from the molten agarose by phenol extraction and ethanol precipitation (Maniatis et al., MOLECULAR CLONING: A LABORATORY MANUAL Cold Spring Harbor Laboratory, Cold Spring Harbor, N.Y., 1982). Plasmid DNA was sequenced using a modification (Hattori et al., *Nucleic Acid Res.* 13:7813–7827, 1985) of the dideoxy method (Sanger et al., *Proc. Nat'l Acad. Sci.* 74:5463–5467, 1977). Reactions were run using the −20 universal primer (New England Biolabs).

TCA precipitation

Aliquots (5 µl) of amplification reactions were quenched in 20 µl 10 mM EDTA and placed on ice until all time point samples had been collected. The quenched samples were then applied to glass filter discs, and immediately dropped into ice-cold 5% trichloroacetic acid ("TCA")-1% sodium pyrophosphate for 10 min with occasional mixing. Two 5 min washes with ice-cold 5% TCA were followed by two additional washes with 95% ethanol and lyophilization to dryness. Radioactivity was determined in a liquid scintillation counter.

Polyacrylamide gel electrophoresis

Samples (1 to 6 µl) were mixed with 4–5 µl formamide dye (90% deionized formamide, 10 mM TrisHCl (PH 8.0), 1 mM EDTA, xylene cyanol and bromophenol blue), and applied to a pre-run 12-cm-long 7% denaturing polyacrylamide gel. Gels were run at 350 volts until the bromophenol blue dye had reached the bottom. In some cases the gels were fixed and dried prior to autoradiography. Fixing involved a 15 min wash in 10% methanol-7% acetic acid. The profiles of the RNA products separated by this procedure were visualized by autoradiography at room temperature.

EXAMPLE 1

Design and Synthesis of Oligonucleotides For a Gag Test System

Figures 2A, 2B:
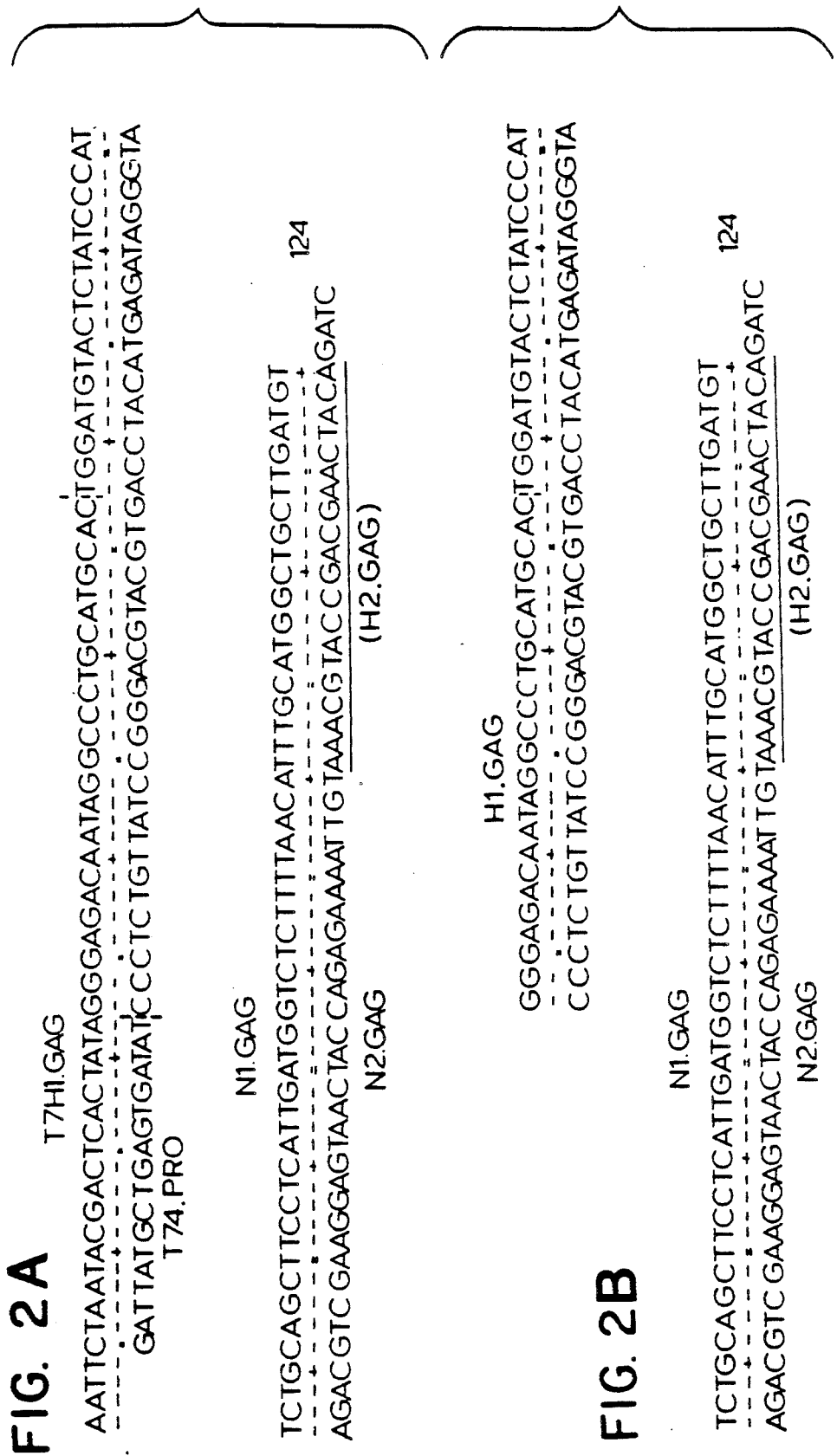
FIG. 2A, the gag test sequence.
FIG. 2B, the gag2 test sequence.

A synthetic DNA sequence (FIG. 2A) was designed to include an EcoRI site, a T7 phage promoter, a sequence required for initiation of transcription by T7 RNA polymerase and a 19 bp hybridization region (hybridization region 1). The 47 b antisense strand oligonucleotide (T7H1.GAG) involved in the cloning of these elements also serves as the first primer. Hybridization region 2 lies 53 bp away from hybridization region 1 and is 20 bp in length. The primer made to this region (H2.GAG) is a 20 b oligonucleotide duplicate of the sense strand and is not used for cloning. The sequence spanning and including the hybridization regions is a 92 bp segment of the gag portion of the HTLV-III genome, the causative agent of AIDS. This particular gene segment was chosen because the primers were predicted to hybridize efficiently and because the distance between the two hybridization regions was relatively short. In addition, a XbaI site was placed at the end of the sequence for cloning ease. The gag test sequence test sequence also contains SphI and PstI sites which can aid in the screening of recombinants.

A total of four oligonucleotides were used in the cloning of this fragment. N1.GAG, used in the construction of both the gag test and the gag2 test sequence, completes the antisense strand and is used only in the cloning process. Similarly, T74.PRO is the sense strand component of the T7 promoter. N2.GAG however, was used in the construction of both test fragments, and has also been used as an intermediate (second template) in two steps of the amplification cycle. The entire cloned gag test fragment can also represent an intermediate of the amplification cycle (third template). Once cloned into an appropriate vector the gag test DNA could be transcribed by T7 RNA polymerase to produce a RNA fragment (first template) useful as an amplification intermediate involved in three of the steps. In addition, T7H1.GAG and H2.GAG serve as primers in the test system.

The gag2 test synthetic DNA fragment (FIG. 2B) does not contain the T7 promoter, but the remainder of the sequence is identical to the gag test sequence and therefore, both N1.GAG and N2.GAG were involved in its construction. The oligonucleotide required to complete the antisense strand is called H1.GAG. Once cloned, the gag2 test fragment can be used as a template for testing amplification, using a DNA restriction fragment as template nucleic acid.

EXAMPLE 2

Construction of the Gag Test Plasmids

The oligonucleotides T74.PRO and N1.GAG (2 µg each), were phosphorylated separately in 20 µl reactions containing 70 mM Tris-HCl (PH 7.6), 10 mM MgCl₂, 5 mM DTT, 0.5 mM ATP and 5 units T4 polynucleotide kinase, at 37° C. for 30 min. Phosphorylated T74.PRO and N1.GAG (10 µl of each) were mixed with 1 µg each of unphosphorylated T7H1.GAG and N2.GAG, and 3 µl 100 mM Tris-HCl (PH7.8)—500 mM NaCl, in a final volume of 29 µl for the gag test assembly. The gag2 test mixture contained 10 µl phosphorylated N1.GAG, 1 µg each of unphosphorylated H1.GAG and N2.GAG, and 1.8 µl 100 mM Tris-HCl (PH 7.8)—500 mM NaCl, in a final volume of 18 µl. The oligonucleotide mixtures were hybridized separately by placing them at 90° C. for 10 min followed by slow cooling to room temperature for 10 to 16 h 60 µl reactions containing 50 mM Tris-HCl (pH 7.8), 10 mM MgCl₂, 20 mM DTT, 1 mM ATP and 50 µg/ml BSA were used to ligate the hybridized oligonucleotides together. 400 units T4 DNA ligase was added to the gag test reaction and it was incubated at 15° C. for 2 h while the gag2 test reaction was incubated for 14 to 16 h with 200 units T4 DNA ligase.

The isolated and purified synthetic DNA segments were mixed with plasmid pUC19 which had been linearized by digestion at restriction enzyme sites within the polylinker region. T4 DNA ligase was used to ligate the gag test sequence into the EcoRI- XbaI fragment of pUC19, while the gag2 test sequence was ligated to the SmaI-XbaI fragment. Plasmid DNA from transformants obtained after these reactions were used to transform *E. coli* were screened by restriction analysis, and the final plasmids (PGAG.TEST and pGAG2.TEST) were determined to be correct by sequence analysis.

EXAMPLE 3

Effect of Primer Concentration on RNA Amplification

The reaction mixtures (25 μl) which were used to amplify RNA transcribed from the gag test oligonucleotides contained 50 mM Tris-HCl (PH 8.45), 6 mM MgCl$_2$, 40 mM KCl, 10 mM dithiothreitol, 0.5 mM NTP (ATP, CTP, GTP, UTP), 1 mM dNTP (dATP, dCTP, dGTP dTTP), 20 units RNasin, 10 units T7 RNA polymerase, 10 units reverse transcriptase, 0.4 units RNase H, and 10 μCi [−32 p] UTP. Two of the reactions contained 0.5 ng (0.015 pmoles) N2.GAG while the other two reactions contained no template. The primers T7H1.GAG and H2.GAG were each added at final concentrations of 3.4 μM or 0.34 μM to reactions containing either N2.GAG or no template. The reactions were incubated at 42° C. for 2 h. Total synthesis of RNA was monitored by determining the incorporation of TCA insoluble cpm at 30 min. intervals. The effect of the primer concentration on template- dependent RNA synthesis is shown in Table 1. Aliquots of each reaction, containing equal amounts of synthesized RNA, were analyzed by PAGE and autoradiography (FIG. 3, lanes 1–4 numbered the same as the reactions).

TABLE 1

RNA amplification from N2.GAG after 2 h.

| Reaction | Concentration of each primer (μM) | Template (ng) | RNA Synthesized (μg) |
|---|---|---|---|
| 1 | 3.4 | 0.5 | 2.8 |
| 2 | 3.4 | — | 2.1 |
| 3 | 0.34 | 0.5 | 1.8 |
| 4 | 0.34 | — | 0.7 |

It was found that while reaction 1 resulted in the greatest incorporation of isotope, the no template control, reaction 2, was also high (73% of reaction 1) and produced a very similar electrophoretic profile. It would therefore appear that in the presence of high primer concentrations, a RNA transcript of identical size to that expected in amplification is produced in the absence of any template. Results using samples with a 10-fold decrease in primer concentration were dramatically different. The amount of RNA produced in reaction 3 was 2.6 times that of reaction 4, but while virtually all of the transcript was found in a single band of the expected size in reaction 3, no fragments greater than 60 to 70 b were found in reaction 4. Primer concentration therefore plays a significant role in the accuracy and efficiency of RNA amplification.

A control RNA transcript used to represent the size of fragment expected to be generated by the amplification system (lane 0 of FIG. 3) was prepared by transcription from the test plasmid. pGAG.TEST was linearized by digestion with XbaI, proteinase K treated (Maniatis et al., MOLECULAR CLONING: A LABORATORY MANUAL Cold Spring Harbor Laboratory, Cold Spring Harbor, N.Y., 1982), phenol extracted and ethanol precipitated. T7 RNA polymerase was then used according to the supplier's recommendations to transcribe 0.5 μg of the resulting fragment in a 25 μl reaction mixture containing 10 μCi [−32 p] UTP.

EXAMPLE 4

Effect of Template Concentration on RNA Amplification

The standard 50 μl reaction mixture used to amplify RNA transcribed from the gag test oligonucleotides contained 0.34 μM T7H1.GAG, 0.34 μM H2.GAG, 50 mM Tris-HCl (PH 8.45), 6 mM MgCl$_2$, 40 mM KCl, 10 mM DTT, 0.5 mM NTP, 1 mM dNTP, 40 units RNasin, 20 units T7 RNA polymerase, 20 units reverse transcriptase, 0.8 units RNase H and 10–20 μCi [−32 p] UTP. The reactions contained amounts of template (N2.GAG) varying from 1 ng to 1 fg. One reaction contained no template. The reactions were incubated at 42° C. for 3 h, during which total synthesis of RNA was monitored by determining the incorporation of TCA insoluble cpm at 30 min intervals. As indicated in Table 2, total RNA synthesis was higher than the no template control for all template concentrations tested. Although the total synthesis of RNA generally decreased with decreasing template concentration, this decrease in synthesis was not quantitative. Thus, the degree of amplification of RNA per starting template generally increased with decreasing template concentration. Amplification of $8 \times 10^8$ fold was achieved by synthesis of 0.8 μg RNA from 1 fg of N2.GAG template. One fg of the 102-b N2.GAG oligonucleotide represents approximately $2 \times 10^4$ molecules.

TABLE 2

RNA amplification from N2.GAG after 3 h.

| Reaction | Template | RNA Synthesized (μg) | Fold amplification |
|---|---|---|---|
| 1 | 1 ng | 3.5 | $3.5 \times 10^3$ |
| 2 | 100 pg | 4.4 | $4.4 \times 10^4$ |
| 3 | 10 pg | 4.1 | $4.1 \times 10^5$ |
| 4 | 1 pg | 3.0 | $3.0 \times 10^6$ |
| 5 | 100 fg | 2.7 | $2.7 \times 10^7$ |
| 6 | 10 fg | 1.9 | $1.9 \times 10^8$ |
| 7 | 1 fg | 0.78 | $7.8 \times 10^8$ |
| 8 | — | 0.046 | — |

Figure 4:
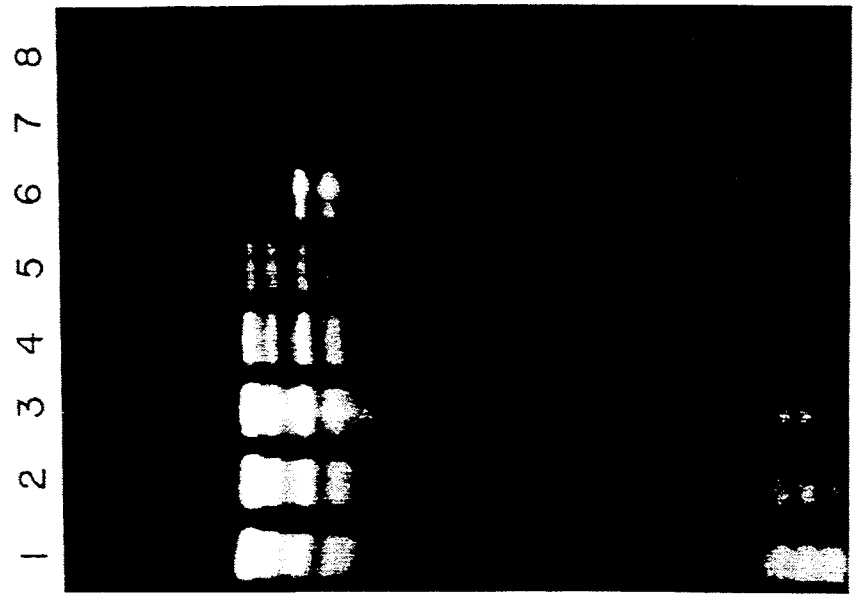
FIG. 4 is an autoradiogram of PAGE analysis of amplification reactions using different template concentrations.

The RNA which was synthesized after a reaction time of 3 h was analyzed by PAGE, for each template concentration (FIG. 4 lanes 1–8, numbered the same as the reactions). A major band representing a RNA of about 100 b was present in all reactions except the ones containing 1 fg template and no template. The reaction containing 1 fg template did not have much of this 100 b product at 3 h but the overall RNA synthesis was higher than and qualitatively different from the no template reaction.

EXAMPLE 5

Hybridization Analysis of RNA Products

Amplification reactions containing amounts of N2.GAG template varying from 1 pg to 0.1 fg were performed following the teaching of example 4, except the radio labeled UTP was omitted. The reactions were incubated at 42° C. for 3 h. Aliquots were removed from each reaction at 30 min intervals and applied to a nylon membrane (Amersham). The nucleic acids that were contained in these reaction aliquots were fixed by exposure to ultraviolet light. The membrane was prehybridized at 50° C. for 1 h in prehybridization buffer consisting of a final concentration of 50% v/v formamide, $5 \times$ SSC and $5 \times$ Denhardt's solution (Maniatis et al, 1982; Southern et al, 1975) at a volume equivalent to 5 mls of solution per 100 cm2 and hybridized with a radio labeled probe with a specific activity of 106 cpm/ml of hybridization solution. Hybridization was performed at 50° C. for 16 h in 50% formamide, 5×SSC and 5×Denhardt's solution (Maniatis et al. MOLECULAR CLONING: A LABORATORY MANUAL Cold Spring Harbor Laboratory, Cold Spring Harbor, N.Y., 1982; Southern et al, Southern, E. (1985) *J. Mol. Biol.* 98:503, 1975). The radio labeled probe was the synthetic oligonucleotide 5'GATCTGGGATAGAG-TACATCCA 3' which had been labeled at the 5' end using T4 polynucleotide kinase and (−32 p) ATP. After the membrane was washed at 50° C. in a series of 2, 3 min. washes consisting of 2×SSC, 0.1% v/v SDS and 0.2×SSC, 0.1% v/v SDS (Southern et al, Souther, E. (1985) *J. Mol. Biol.* 98:503, 1975; Maniatis et al, MOLECULAR CLONING: A LABORATORY MANUAL Cold Spring Harbor Laboratory, Cold Spring Harbor, N.Y., 1982; Szostak et al. *Methods in Enzymol.* 68:419, 1979).

Figure 5:
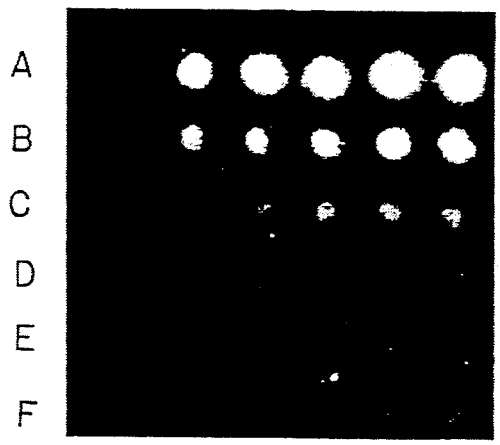
FIG. 5 is an autoradiogram of Dot-blot hybridization on amplification reactions.

FIG. 5 shows the results of the hybridization analysis performed on the amplification reactions, containing various amounts of N2.GAG template, which were sampled at different times of incubation.

Each column of FIG. 5 represents a different time point (1, 30 min; 2, 60 min; 3, 90 min; 4, 120 min; 5, 150 min; 6, 180 min) and each row represents a different amount of added N2.GAG template (1, 1 pg; 2, 100 fg; 3, 10 fg; 4, 1 fg; 5, 0.1 fg; 6, no template). Amplification of nucleic acids which hybridized to the labeled probe were observed for rows 1–3 (1 pg–10 fg), however the hybridization to specific nucleic acids in rows 4–5 (1 fg, 0.1 fg) was not higher than row 6 (no template). The apparent non-specific binding of labeled probe in row 6 seems to be related to DNA or RNA synthesis since the hybridization signal increases with increasing time.

EXAMPLE 6

Use of DNA Restriction Fragment as Template

The plasmid pGAG2.TEST was digested with MspI, treated with proteinase K, purified by phenol extraction and ethanol precipitation, and denatured by boiling for 5 min. Amplification reactions were performed and analyzed following the teaching of Example 4, except the MspI digested pGAG2.TEST was used as a template instead of the N2.GAG oligonucleotide. The amounts of plasmid added to each reaction varied from 55 ng to 5.5 pg, and no template. To simulate additional DNA which would be present in an actual sample, alternate reactions contained 1 ng of calf thymus DNA which had been similarly digested, purified and denatured. After a 3 h incubation at 42° C., the synthesis of RNA was determined by TCA precipitation and PAGE analysis. As indicated in Table 3, total RNA synthesis was higher than the no template controls for all template concentrations tested. The degree of amplification was calculated based on RNA synthesis from the actual template which was 1.8% of the total plasmid DNA.

The total RNA synthesis (degree of amplification) from a particular initial level template concentration was consistently lower for the restriction fragment (Table 3) as compared to that for the synthetic oligonucleotide template (Table 2). This could be due to competition with the complementary strand of the restriction fragment template under the conditions used.

TABLE 3

| | RNA Amplification From MspI-Digested pGAG2.TEST | | |
|---|---|---|---|
| Reaction | Template* | RNA Synthesized** | Fold amplification** |
| 51 | 55.0 ng [1 ng] | 3.65 | 3.7 × 103 |
| 2 | | (4.05) | (4.1 × 103) |
| 3 | 5.5 ng [100 pg] | 3.54 | 3.5 × 104 |
| 4 | | (3.16) | (3.2 × 104) |
| 5 | 550.0 pg [10 pg] | 2.29 | 2.3 × 105 |
| 106 | | (2.79) | (2.8 × 105) |
| 7 | 55.0 pg [1 pg] | 2.62 | 2.6 × 106 |
| 8 | | (0.67) | (0.7 × 106) |
| 9 | 5.5 pg [100 fg] | 1.37 | 1.4 × 107 |
| 10 | | (2.26) | (2.3 × 107) |
| 1511 | | 1.25 | |
| 12 | | (0.08) | |

*Numbers in brackets indicate equivalent amounts of N2.GAG.
**Numbers in parentheses indicate RNA synthesis in presences of 1 μg MspI-digested calf thymus DNA.

Figure 6:
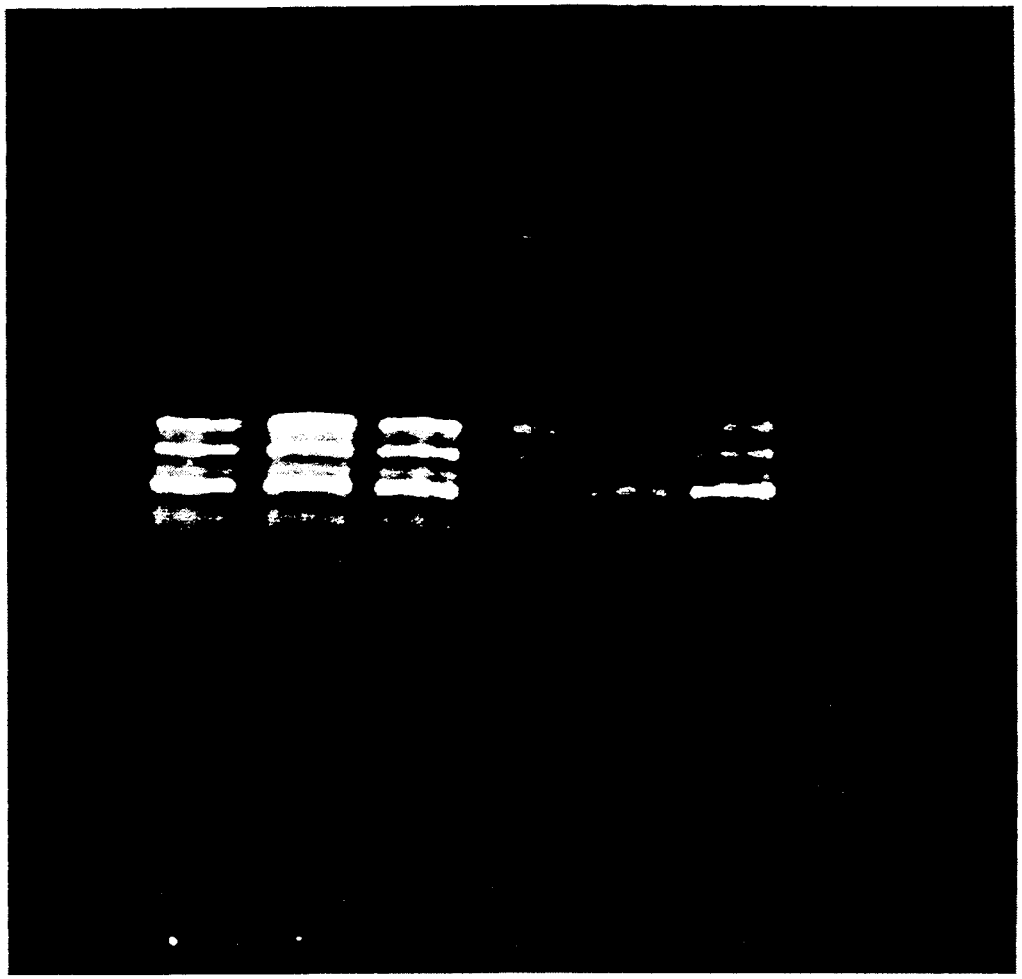
FIG. 6 is an autoradiogram of PAGE analysis of amplification reaction using restriction fragments as template.

The RNA which was synthesized after a reaction time of 3 h was analyzed by PAGE (FIG. 6, lanes 1–6, 11 and 12, numbered the same as the reactions). The major band representing a RNA of about 100 b was present in reactions (lanes 1–6 but absent in the no template reactions (lanes 11 and 12). The RNA in lane 0 was a standard, which was prepared following the reaching of Example 3. There was no apparent qualitative difference in he synthesized RNA either with (lanes 2, 4 and 6) or without (lanes 1, 3, and 5) the additional of 1 μg of MspI-digested calf thymus DNA.

EXAMPLE 7

Use of RNA Fragment as Template

The plasmid pGAG2.TEST is digested with XbaI, treated with proteinase K, and purified by phenol extraction and ethanol precipitation. RNA of a sequence complementary to N2.GAG is transcribed from the linearized pGAG.TEST plasmid using T7 RNA polymerase. The resulting RNA is purified by digestion with DNase (ProMega BioTec, Madison, Wis.), followed by phenol extraction and ethanol precipitation. The purified RNA is used as a template for amplification reactions following the teaching of Example 5. amounts of RNA are added to each reaction and vary from 55 ng to 5.5 pg, and no template. After a 3 h incubation at 42° C., the synthesis of specific RNA is determined by hybridization to labeled oligonucleotide probe, following the teaching of Example 5.

EXAMPLE 8

Use of Ribosomal RNA as a Template Amplification of Internal Sequences

Two primers are used for amplifying RNA sequences which are complementary to a part of *E. coli* 16S ribosomal RNA (rRNA). One of these primers T7HIRIB3.PR2 (AATTCTAATACGACTCAC-TATAGGGAGTATTACCGCGGCTGCTG) contains the antisense strand of the T7 promoter and initiation site, and a sequence which is complementary to 16S rRNA. The other RIB8.PR (AATACCTTTGCT-CATTGACG) is complementary to the DNA synthesized by using T7H1RIB3.PR2 as a primer and 16S rRNA as a template. A third synthetic oligonucleotide RIB5.PR (AGAAGCACCGGCTAAC) which allows detection of amplification is complementary to the RNA products of the amplification reaction, which are in turn complementary to the original rRNA template.

Reaction mixtures (25 μl) contain 50 mM Tris-HCl (PH 8.45), 6 mM MgCl$_2$, 40 mM KCl, 10 mM DTT, 0.5 mM NTP, 1 mM dNTP, 20 units RNasin, 10 units T7 RNA polymerase, 10 units AMV reverse transcriptase, 0.4 units RNase H, 0.34 μm T7H1RIB3.PR2, and 0.34 μm RIB8.PR.

Amounts of *E. coli* rRNA varying from 50 ng to 50 fg are added to the reactions. One reaction contains no added rRNA. The reactions are incubated at 42° for 3 h, during which aliquots are removed at 30, 60, 120, and 180 minutes. The reaction aliquots are quenched, fixed up to a nylon membrane, and hybridized to the 32 p 5'-end labeled RIB5.PR probe, following the teaching of Example 5.

EXAMPLE 9

Use of Ribosomal RNA as a Template Amplification of 5'-Terminal Sequences

Two primers are used for amplifying RNA sequences which are homologous to a part of *E. coli* 16S rRNA. One of these primers RIB12.PR (TTACT-CACCCGTCCGCC) is complementary to 16S rRNA. The other T7H1RIB5.PR (AATTCTAATACGACT-CACTATAGGGAGAAATTGAAGAGTTTGAT-CAT) is complementary to the 3' end of the DNA synthesized by using RIB12.PR as a primer and 16S rRNA as a template. A third synthetic oligonucleotide RIB11.PR (GTTCGACTTGCATGTGT-TAGGCCTGCCGCCAGCGTTCAATCTGAGCC) which allows detection of amplification is complementary to both the RNA products of the amplification and the original rRNA template. The amplification reactions for rRNA and detection of the synthesized RNA are performed following the teaching of Example 8, except that T7H1RIB5.PR and RIB12.PR are used as primers (in place of T7H1RIB3.PR2 and RIB8.PR) and RIB11.PR is used as an oligonucleotide probe (in place of RIB5.PR).

Although preferred embodiments of the invention have been described in detail, it will be understood by those skilled in the art that variations may be made thereto without departing from either the spirit of the invention or the scope of the appended claims.

EXAMPLE 10

Specific Enhancement of Nucleic Acid Amplification Using Dimethylsulfoxide (DMSO) and Bovine Serum Albumin (BSA)

The nucleic acid amplification process, as exemplified in the above examples, was used with the following bacterial strains, plasmids and RNA template were used. A pGEM-3-pol plasmid and an pUC-pol plasmid each containing a 1450 base pair restriction fragment from HIV 1 (strain HxB2) were constructed from a BamH1EcoR1 subclone obtained as a gift from Dr. R. Gallo (NCI, NIH, Bethesda, Md.). This restriction fragment contains a portion of the HIV1 gag gene and the majority of the HIV 1 pol gene. *E. coli* strain HB101 was transformed with either the pGEM-3-pol plasmid on the pUC-pol plasmid. Plasmid DNA was prepared by methods described in Maniatis et al. MOLECULAR CLONING A LABORATORY MANUAL p. 86 Cold Spring Harbor Laboratory.

To obtain pol-RNA template, the pGEN-3-pol plasmid was linearized with EcoR1, extracted with phenol-chloroform, and precipitated in ethanol. EcoR1 cuts uniquely at the end of the inserted pol DNA. Purified DNA was transcribed using SP6 RNA polymerase (a suitable RNA polymerase is available from Promega, Madison, Wis.) according to the method of Melton et al. *Nucleic Acids Res* 12:7035 (1984). 5 units of RNase-free DNase I (a suitable DNase I is also available from Promega, Madison, Wis.) was added and the mixture incubated at 37° C. for 15 minutes. The RNA product was extracted with phenol-chloroform and precipitated with ethanol. The yield of RNA was determined spectrophotometrically.

Figure 7:
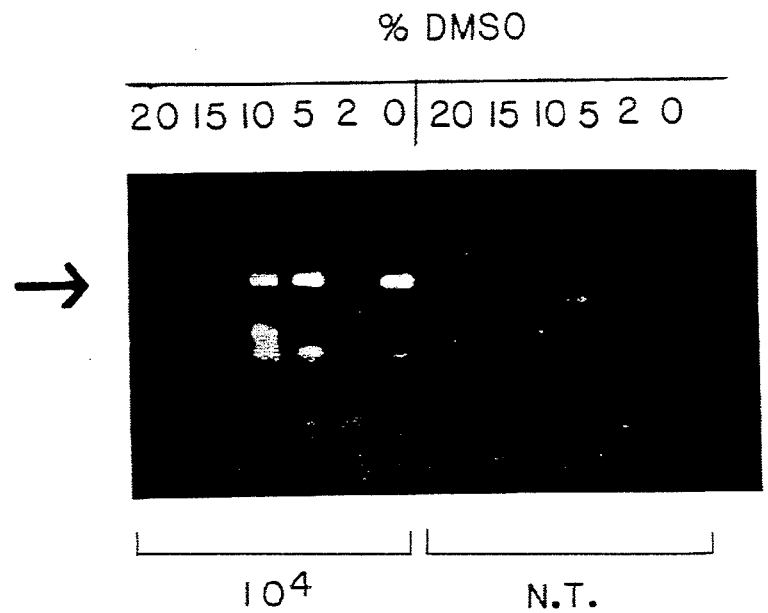
FIG. 7 is an ethidium bromide stained agarose gel for a titration of amplification reactions with no HIV target sequence (no template) using 0–20% DMSO showing effect on non-specific products (NSPs).
Figure 8:
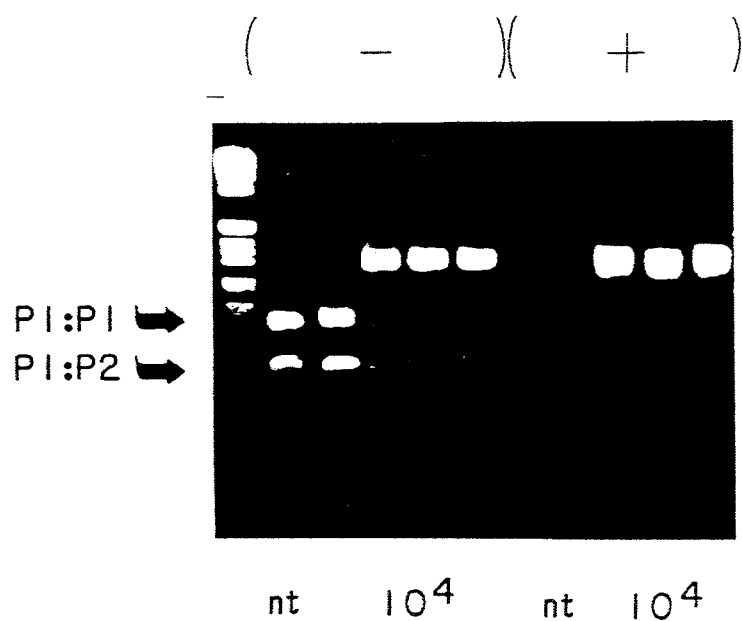
FIG. 8 is an ethidium bromide stained agarose gel of amplification reactions with no template (nt) and $10^4$ copies of template using 0% (−) and 15% (+) DMSO showing elimination of NSPs.

The inclusion of DMSO at a final concentration of between 0% and 20% to the reaction mixture used for amplification, as shown in FIG. 7, resulted in a decrease of non-specific products (NSP) from the non-productive side reactions. FIG. 8 shows that two types of NSPs designated P1:P1 and P1:P2 were eliminated from the non-target sequence containing samples with the use of 15% DMSO in the reaction medium.

Figure 9:
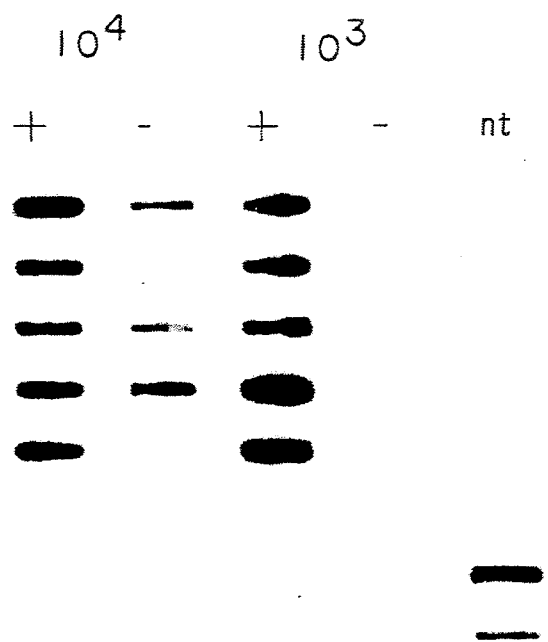
FIG. 9 is an autoradiogram of a slot-blot hybridization analysis of amplification reactions using 0% (−) and 15% (+) DMSO with no template (nt) and $10^3$ and $10^4$ template copies, showing increased reproducibility and sensitivity.

The presence of DMSO in the reaction medium at 15% had the further effect of improving reproducibility of sample run through the claimed amplification process as demonstrated in the slot-blot shown in FIG. 9. $10^3$ and $10^4$ copies of a target sequence were used and the DMSO (indicated by "+") improved the reproducibility as shown by the 5 bands in each lane, but also the sensitivity as shown by comparison of the "+" and "−" lanes under $10^3$ copies of target sequence.

Figure 10B:
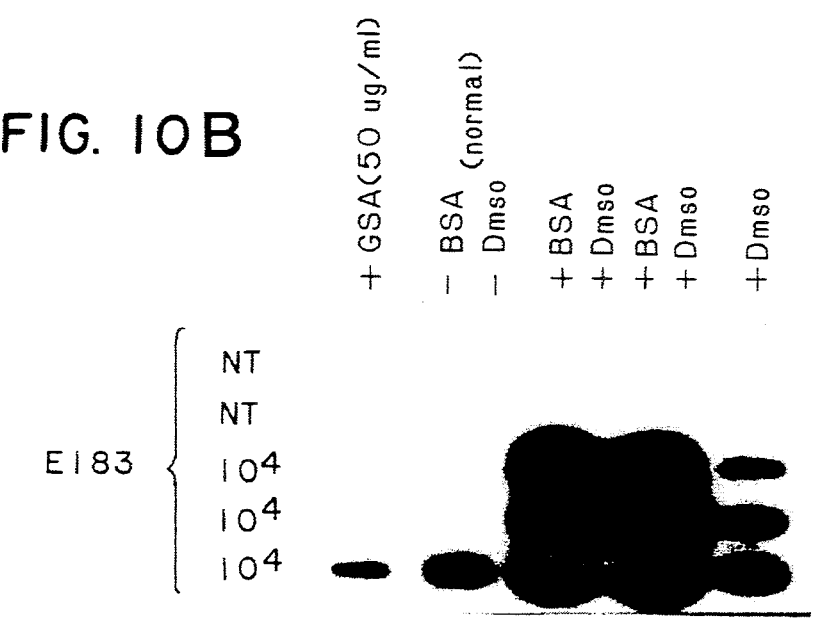
FIG. 10B is an autoradiogram of a slot-blot hybridization analysis of amplification reactions with no template (nt) and $10^4$ copies of template using 50 µg/ml BSA, 0% DMSO and 0% BSA, 15% DMSO and 50 µg/ml BSA, 15% DMSO and 100 µg/ml BSA, and 15% DMSO showing increased sensitivity of the combination of BSA and DMSO for detection of amplified template, and for increased reproducibility using DMSO alone.
Figure 10A:
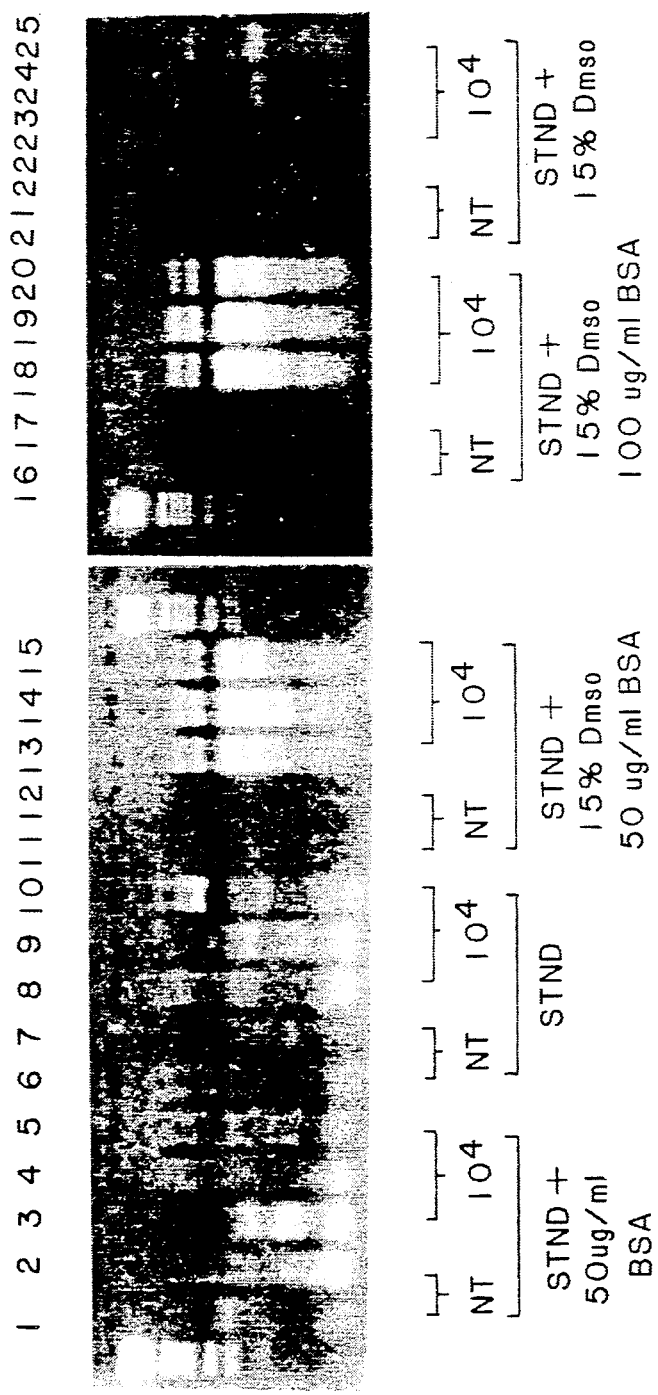
FIG. 10A is an ethidium bromide stained agarose gel of amplification reactions with no template (nt) and $10^4$ copies of template using 50 µg/ml BSA, 0% DMSO and 0% BSA, 15% DMSO and 50 µg/ml BSA, 15% DMSO and 100 µg/ml BSA, and 15% DMSO showing increased sensitivity of the combination of BSA and DMSO for detection of amplified template.

When DMSO and BSA (a suitable BSA is available from Boehringer Mannheim, Indianapolis, Ind., as special quality for molecular biology) were both used in the reaction medium, the sensitivity and reproducibility were significantly increased, as exemplified in FIGS. 10A and 10B, which show an increase in amplification of $10^4$ copies of a target sequence and both an increase in sensitivity and reproducibility, respectively. Concentrations of 50 μg/ml and 100 μg/ml BSA were used with a final concentration of DMSO of 15%. An increase in amplification of at least 100 fold was obtained over the reaction medium without DMSO and BSA, and higher increases were suggested up to $10^8$ fold and detection and isolation of as low as a single copy of target were also suggested by the results.

Figure 11:
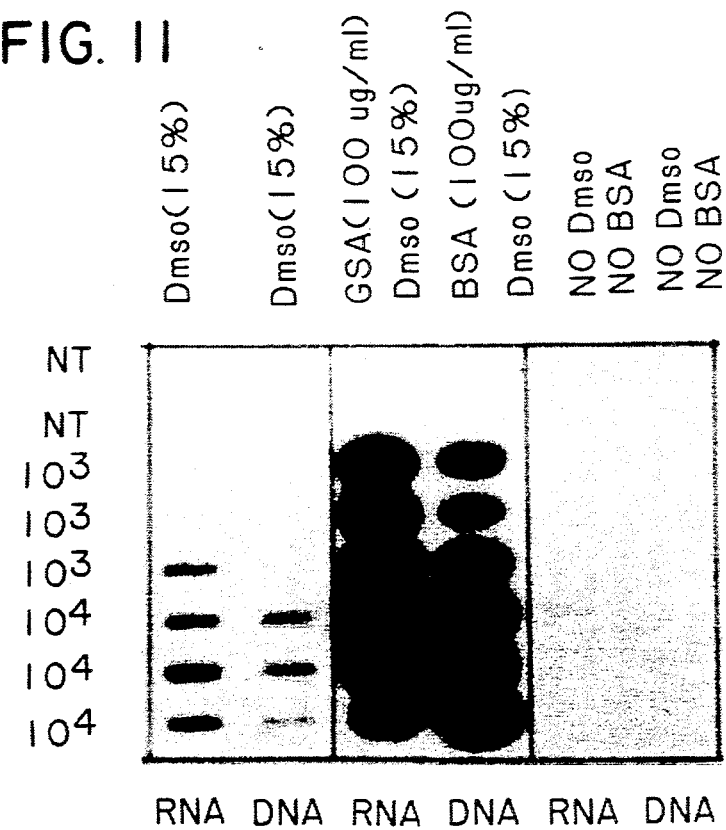
FIG. 11 is an autoradiogram of a slot-blot hybridization analysis of amplification reactions with no template (nt) and $10^3$ and $10^4$ copies of template using 15% DMSO alone and 15% DMSO and 100 µg/ml BSA showing increased sensitivity of the combination of BSA and DMSO for detection of amplified template, and for increased reproducibility using DMSO alone.

The amplification of both RNA and DNA relative to the presence and absence of DMSO and BSA and to relative to copy number of a target sequence is shown in the slot-blot autoradiogram depicted in FIG. 11. Both RNA and DNA were amplified with increased sensitivity and reproducibility using DMSO and BSA in the reaction mixture.

What is claimed is:

1. A process for the amplification of a specific nucleic acid sequence, at a relatively constant temperature and without serial addition of reagents, comprising the steps of:
   (A) providing a single reaction medium containing reagents comprising
   (i) a first oligonucleotide primer,
   (ii) a second oligonucleotide primer comprising an antisense sequence of a promoter,
   (iii) a DNA-directed RNA polymerase that recognizes said promoter,
   (iv) an RNA-directed DNA polymerase,
   (v) a DNA-directed DNA polymerase,
   (vi) a ribonuclease that hydrolyzes RNA of an RNA-DNA hybrid without hydrolyzing single- or double-stranded RNA or DNA, (vii) ribonucleoside and deoxyribonucleoside triphosphates, and
(vi) dimethylsulfoxide; and then
(B) providing in said reaction medium RNA comprising an RNA first template which comprises said specific nucleic acid sequence or a sequence complementary to said specific nucleic acid sequence, under conditions such that a cycle ensues wherein
  (i) said first oligonucleotide primer hybridizes to said RNA first template,
  (ii) said RNA-directed DNA polymerase uses said RNA first template to synthesize a DNA second template by extension of said first oligonucleotide primer and thereby forms an RNA-DNA hybrid intermediate,
  (iii) said ribonuclease hydrolyzes RNA which comprises said RNA-DNA hybrid intermediate,
  (iv) said second oligonucleotide primer hybridizes to said DNA second template,
  (v) said DNA-directed DNA polymerase uses said second oligonucleotide primer as template to synthesize said promoter by extension of said DNA second template; and
  (vi) said DNA-directed RNA polymerase recognizes said promoter and transcribes said DNA second template, thereby providing copies of said RNA first template;
and thereafter
(C) maintaining said conditions for a time sufficient to achieve a desired amplification of said specific nucleic acid sequence.

2. A process according to claim 1, wherein said RNA first template comprises said specific nucleic acid sequence and wherein step (B) comprises providing single-stranded RNA in said reaction medium such that
  (i) said first oligonucleotide primer hybridizes to said single-stranded RNA,
  (ii) said RNA-directed DNA polymerase uses said single-stranded RNA as a template to synthesize a DNA second template by extension of said first oligonucleotide primer and thereby forms an RNA-DNA hybrid,
  (iii) said ribonuclease hydrolyses RNA which comprises said RNA-DNA hybrid,
  (iv) said second oligonucleotide primer hybridizes to said DNA second template,
  (v) said DNA-directed DNA polymerase uses said second oligonucleotide primer as template to synthesize said promoter by extension of said DNA second template; and
  (vi) said DNA-directed RNA polymerase recognizes said promoter and transcribes said DNA second template, thereby providing copies of said RNA first template.

3. A process according to claim 1, wherein said RNA first template comprises a sequence complementary to said specific nucleic acid sequence and wherein step (B) comprises providing single-stranded RNA in said reaction medium such that
  (i) said second oligonucleotide primer hybridizes to said single-stranded RNA,
  (ii) said RNA-directed DNA polymerase uses said RNA as a template to synthesize a complementary DNA by extension of said second oligonucleotide primer and thereby forms an RNA-DNA hybrid,
  (iii) said ribonuclease hydrolyses RNA which comprises said RNA-DNA hybrid,
  (iv) said first oligonucleotide primer hybridizes to said complementary DNA,
  (v) said DNA-directed DNA polymerase uses said complementary DNA as template to synthesize said DNA second template and said promoter by extension of said first oligonucleotide primer; and
  (vi) said DNA-directed RNA polymerase recognizes said promoter and transcribes said DNA second template, thereby providing copies of said RNA first template.

4. A process according to claim 1, wherein step (B) comprises adding to said reaction medium single-stranded DNA which comprises an antisense sequence of said promoter, such that
  (i) said first oligonucleotide primer hybridizes to said single-stranded DNA,
  (ii) said DNA-directed DNA polymerase uses said single-stranded RNA as a template to synthesize said DNA second template and said promoter by extension of said first oligonucleotide primer; and
  (iii) said DNA-directed RNA polymerase recognizes said promoter and transcribes said DNA second template, thereby providing copies of said RNA first template.

5. A process according to claim 4, wherein step (B) comprises adding to said reaction medium and RNA-DNA hybrid comprising said single-stranded DNA, such that said ribonuclease hydrolyzes RNA which comprises said RNA-DNA hybrid.

6. A process according to claim 1, wherein step (B) comprises adding to said reaction medium single-stranded DNA which comprises said DNA second template, such that
  (i) said second oligonucleotide primer hybridizes to said single-stranded DNA,
  (ii) said DNA-directed DNA polymerase uses said second oligonucleotide primer as template to synthesize said promoter by extension of said DNA second template; and
  (iii) said DNA-directed RNA polymerase recognizes said promoter and transcribes said DNA second template, thereby providing copies of said RNA first template.

7. A process according to claim 6, wherein step (B) comprises adding to said reaction medium and RNA-DNA hybrid comprising said single-stranded DNA, such that said ribonuclease hydrolyzes RNA which comprises said RNA-DNA hybrid.

8. A process according to claim 2, wherein step (B) comprises adding to said reaction medium a DNA comprising said promoter, such that said DNA-directed RNA polymerase transcribes said DNA, thereby synthesizing said single-stranded RNA.

9. A process according to claim 3, wherein step (B) comprises adding to said reaction medium a DNA comprising said promoter, such that said DNA-directed RNA polymerase transcribes said DNA, thereby synthesizing said single-stranded RNA.

10. A process according to claim 1, wherein said second oligonucleotide primer further comprises an antisense sequence of a transcription initiation site for said DNA-directed RNA polymerase, said antisense sequence of said transcription initiation site being operatively linked to said antisense sequence of said promoter.

11. A process according to claim 10, wherein said DNA-directed RNA polymerase is bacteriophage T7 RNA polymerase and wherein said antisense sequence of a transcription initiation site and said antisense sequence of said promoter together comprise the nucleotide sequence

AATTCTAATACGACTCACTATAGGGAG.

12. A process according to claim 1, wherein step (B) further comprises adding a sample to said reaction medium under conditions such that, if said sample thereby provides RNA comprising an RNA first template which comprises said specific nucleic acid sequence or a sequence complementary to said specific nucleic acid sequence, said cycle ensues, and wherein said process further comprises, after step (C), a step (D) of monitoring said reaction medium for consumption of any of said reagents (i), (ii) and (vii) or for accumulation of any product of said cycle.

13. A process according to claim 12, wherein step (D) comprises detecting a nucleic acid product of said cycle.

14. A process according to claim 13, wherein step (D) comprises detecting said nucleic acid product using a nucleic acid probe.

15. A process according to claim 13, wherein step (D) comprises detecting said nucleic acid product using restriction endonucleases and electrophoretic separation.

16. A process according to claim 13, wherein step (D) comprises monitoring the accumulation of said RNA first template.

17. A process according to claim 13, wherein step (D) comprises monitoring the accumulation of said DNA second template.

18. A process according to claim 13, wherein step (D) comprises monitoring DNA containing said promoter.

19. A process according to claim 13, wherein step (D) comprises monitoring the accumulation of said RNA-DNA hybrid intermediate.

20. A process according to claim 13, wherein step (D) further comprises comparing consumption of any reagent of said reagents (i), (ii) and (vii) or accumulation of any product of said cycle with a value representing consumption of said reagent or accumulation of said product in said reaction medium in the absence of said specific nucleic acid sequence and said sequence complementary thereto.

21. A process according to claim 1, wherein said ribonuclease comprises *Escherichia coli* ribonuclease H.

22. A process according to claim 1, wherein said ribonuclease comprises calf thymus ribonuclease H.

23. A process according to claim 1, wherein said first oligonucleotide primer to said second oligonucleotide primer is bound reversibly to an immobilized support.

24. A process according to claim 1, wherein said DNA-directed RNA polymerase is a bacteriophage RNA polymerase.

25. A process according to claim 24, wherein said DNA-directed RNA polymerase is bacteriophage T7 RNA polymerase.

26. A process according to claim 24, wherein said DNA-directed RNA polymerase is bacteriophage T3 polymerase.

27. A process according to claim 24, wherein said DNA-directed RNA polymerase is bacteriophage φII polymerase.

28. A process according to claim 24, wherein said DNA-directed RNA polymerase is Salmonella bacteriophage sp6 polymerase.

29. A process according to claim 24, wherein said DNA-directed RNA polymerase is Pseudomonas bacteriophage gh-1 polymerase.

30. A process according to claim 1, wherein said RNA-directed DNA polymerase is a retrovirus reverse transcriptase.

31. A process according to claim 30, wherein said retrovirus reverse transcriptase is avian myeloblastosis virus polymerase.

32. A process according to claim 30, wherein said retrovirus reverse transcriptase is a Moloney murine leukemia virus polymerase.

33. A process according to claim 1, wherein said DNA-directed DNA polymerase lacks exonuclease activity.

34. A process according to claim 1, wherein all DNA polymerases in said reaction medium lack exonuclease and DNA endonuclease activity.

35. A process according to claim 1, wherein said DNA-directed DNA polymerase is avian myeloblastosis virus polymerase.

36. A process according to claim 1, wherein said DNA-directed DNA polymerase is DNA polymerase $\alpha$ or DNA polymerase $\beta$.

37. A process according to claim 1, wherein said DNA directed DNA polymerase is calf thymus DNA polymerase.

38. A process according to claim 1, wherein step (C) comprises maintaining said conditions for a time between 30 minutes and 4 hours.

39. A process according to claim 1, further comprising the steps of ligating a DNA product of said cycle into a cloning vector and then cloning said DNA product.

40. A process according to claim 39, further comprising the step of expressing a product encoded by said DNA product of said cycle in an expression system.

41. A process according to claim 1, wherein said dimethylsulfoxide is provided at a final concentration in the range of 2–15%.

42. A process according to claim 41, wherein said dimethylsulfoxide is provided at a final concentration of about 15%.

43. A process according to claim 1, wherein said single reaction medium of step (A) further comprises bovine serum albumin.

44. A process according to claim 43, wherein said bovine serum albumin is provided at a final concentration in the range of 50–500 μg/ml.

45. A process according to claim 1, wherein said dimethylsulfoxide is provided at a final concentration of about 15% and said single reaction medium of step (A) further comprises bovine serum albumin provided at a final concentration in the range of 50–500 μg/ml.

46. A kit for amplifying nucleic acid sequences, comprising an assemblage of:
(a) a receptacle containing a first oligonucleotide primer,
(b) a receptacle containing a second oligonucleotide primer comprising an antisense sequence of a promoter,
(c) a receptacle containing a ribonuclease that hydrolyses RNA of an RNA/DNA hybrid without hydrolyzing single- or double-stranded RNA or DNA,
(d) a receptacle containing an RNA-directed DNA polymerase, (e) a receptacle containing an DNA-directed RNA polymerase,
(f) a receptacle containing an DNA-directed DNA polymerase,
(g) a receptacle containing ribonucleoside triphosphates,
(h) a receptacle containing deoxyribonucleoside triphosphates, and
(i) a receptacle containing dimethylasulfoxide.

47. A kit according to claim 46, further comprising a receptacle containing bovine serum albumin.

* * * * *

UNITED STATES PATENT AND TRADEMARK OFFICE
CERTIFICATE OF CORRECTION

PATENT NO. : 5,130,238
DATED : July 14, 1992
INVENTOR(S) : Lawrence T. MALEK, Cheryl DAVEY, Graham HENDERSON, Roy SOOKNANAN It is certified that error appears in the above-identified patent and that said Letters Patent is hereby corrected as shown below:

Column 24, line 18, "RNA" should read --DNA--.

Column 24, line 26 "and" should read --an--.

Column 24, line 54 "and" should read --an--.

Column 28, line 3 "dimethylasulfoxide" should read --dimethylsulfoxide--.

Signed and Sealed this

Thirtieth Day of November, 1993

Attest:

BRUCE LEHMAN

Attesting Officer

Commissioner of Patents and Trademarks